US011386555B2

(12) United States Patent
Wilson et al.

(10) Patent No.: US 11,386,555 B2
(45) Date of Patent: Jul. 12, 2022

(54) ASSESSMENT OF ARTERIAL CALCIFICATIONS

(71) Applicant: Case Western Reserve University, Cleveland, OH (US)

(72) Inventors: David L. Wilson, Cleveland Heights, OH (US); Di Wen, San Jose, CA (US); Brendan L. Eck, Cleveland Heights, OH (US); Jacob Levi, Univeristy Heights, OH (US); Yingnan Song, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 202 days.

(21) Appl. No.: 16/797,303

(22) Filed: Feb. 21, 2020

(65) Prior Publication Data

US 2020/0273167 A1 Aug. 27, 2020

Related U.S. Application Data

(60) Provisional application No. 62/808,444, filed on Feb. 21, 2019.

(51) Int. Cl.
*G06T 7/00* (2017.01)
*G06T 7/62* (2017.01)
(Continued)

(52) U.S. Cl.
CPC .......... *G06T 7/0012* (2013.01); *G06K 9/6268* (2013.01); *G06N 20/00* (2019.01); *G06T 3/4053* (2013.01); *G06T 7/33* (2017.01); *G06T 7/38* (2017.01); *G06T 7/62* (2017.01); *G06V 10/40* (2022.01); *G16H 50/30* (2018.01); *G06T 2207/10081* (2013.01);
(Continued)

(58) Field of Classification Search
CPC ....... G06T 7/0012; G06T 7/62; G06T 3/4053; G06T 2207/10081; G06T 2207/20081; G06T 2207/20084; G06T 2207/30101; G06T 2211/424; G16H 50/30; G06N 20/00; G06K 9/46; G06K 9/6268
See application file for complete search history.

(56) References Cited

U.S. PATENT DOCUMENTS 7,657,299 B2 * 2/2010 Huizenga ................ C23F 11/08
600/410
8,970,578 B2 * 3/2015 Voros ...................... A61B 6/504
382/128

(Continued)

FOREIGN PATENT DOCUMENTS

WO WO-2019051358 A1 * 3/2019 ............. G16H 30/40

*Primary Examiner* — Gregory M Desire
(74) *Attorney, Agent, or Firm* — Eschweiler & Potashnik, LLC

(57) ABSTRACT

Embodiments discussed herein facilitate employing a pretrained model to determine risk(s) of adverse event(s) based on Computed Tomography (CT) image volume(s) of an artery and/or training a model to determine such risk(s). Example embodiments can determine risk based on territory-specific calcium score(s) and/or intensity/morphological/location features discussed herein. Various embodiments can determine risk(s) based on a single CT image volume and/or change(s) in CT image volumes taken over a series of time points.

23 Claims, 15 Drawing Sheets

(51) Int. Cl.
  *G06T 7/38*     (2017.01)
  *G06T 7/33*     (2017.01)
  *G06T 3/40*     (2006.01)
  *G06N 20/00*    (2019.01)
  *G16H 50/30*    (2018.01)
  *G06K 9/62*     (2022.01)
  *G06V 10/40*    (2022.01)

(52) U.S. Cl.
  CPC ............ *G06T 2207/20081* (2013.01); *G06T 2207/20084* (2013.01); *G06T 2207/30101* (2013.01); *G06T 2211/424* (2013.01)

(56) References Cited

U.S. PATENT DOCUMENTS

| | | | | |
|---|---|---|---|---|
| 9,152,761 | B2* | 10/2015 | Bhatia | G06K 9/6267 |
| 10,357,218 | B2* | 7/2019 | Wang | G06T 7/0014 |
| 10,368,822 | B2* | 8/2019 | Palma | A61B 6/4435 |
| 10,395,773 | B2* | 8/2019 | Tang | G06K 9/6267 |
| 10,869,644 | B2* | 12/2020 | Zhao | G06T 7/187 |
| 2006/0051814 | A1* | 3/2006 | Jackowski | G01N 33/6896 |
| | | | | 435/7.1 |
| 2019/0138694 | A1* | 5/2019 | Tang | G06T 7/136 |
| 2020/0273167 | A1* | 8/2020 | Wilson | G06K 9/6268 |

\* cited by examiner

```
         ┌──────────────────────────────────────────────────────┐
  210 ─→ │ OBTAIN SET OF CT IMAGE VOLUMES OF ONE OR MORE        │
         │ ARTERIES (E.G., CARDIAC CALCIUM SCORE CT VOLUME      │
         │ IMAGING) FROM DIFFERENT TIME POINTS                  │
         └──────────────────────────────────────────────────────┘
                                  │
                                  ▼
         ┌──────────────────────────────────────────────────────┐
  220 ─→ │ CALCULATE TERRITORY CALCIUM SCORE FOR ONE OR         │
         │ MORE TERRITORIES FOR EACH IMAGE VOLUME OF SET        │
         └──────────────────────────────────────────────────────┘
                                  │
                                  ▼
         ┌──────────────────────────────────────────────────────┐
  230 ─→ │ EXTRACT ICmore FEATURES IN CALCIFIED REGION(S)       │
         │ FROM EACH IMAGE VOLUME OF SET                        │
         └──────────────────────────────────────────────────────┘
                                  │
                                  ▼
         ┌──────────────────────────────────────────────────────┐
  240 ─→ │ PERFORM REGISTRATION OF THE IMAGE VOLUMES            │
         │ FOR EACH TIME POINT                                  │
         └──────────────────────────────────────────────────────┘
                                  │
                                  ▼
         ┌──────────────────────────────────────────────────────┐
  250 ─→ │ ANALYZE CHANGES IN ICmore FEATURES FROM              │
         │ DIFFERENT IMAGE VOLUMES OVER TIME POINTS             │
         └──────────────────────────────────────────────────────┘
                                  │
                                  ▼
         ┌──────────────────────────────────────────────────────┐
  260 ─→ │ PREDICT RISK OF ADVERSE EVENT BASED ON               │
         │ ANALYZED CHANGES IN ICmore FEATURES                  │
         └──────────────────────────────────────────────────────┘
```

FIG. 2

```
    ┌─────────────────────────────────────────────────┐
310─┤ OBTAIN IMAGE VOLUME OF ONE OR MORE ARTERIES     │
    │ (E.G., CARDIAC CALCIUM SCORE CT VOLUME IMAGING) │
    └─────────────────────────────────────────────────┘
                         │
    ┌─────────────────────────────────────────────────┐
320─┤ OBTAIN KNOWN CLINICAL OUTCOME ASSOCIATED WITH   │
    │ PATIENT (E.G., ADVERSE CARDIOVASCULAR EVENT)    │
    └─────────────────────────────────────────────────┘
                         │
    ┌─────────────────────────────────────────────────┐
330─┤ OPTIONALLY PERFORM PRE-PROCESSING ON CT         │
    │ IMAGING TO IMPROVE CT IMAGE VOLUME              │
    └─────────────────────────────────────────────────┘
                         │
    ┌─────────────────────────────────────────────────┐
340─┤ IDENTIFY ONE OR MORE CALCIFICATION CANDIDATE    │
    │ REGIONS BASED ON IMAGE VOLUME                   │
    └─────────────────────────────────────────────────┘
                         │
    ┌─────────────────────────────────────────────────┐
350─┤ EXTRACT ICmore FEATURES IN CALCIFIED REGION(S)  │
    └─────────────────────────────────────────────────┘
                         │
    ┌─────────────────────────────────────────────────┐
360─┤ TRAIN ML/DL MODEL BASED ON EXTRACTED ICmore     │
    │ FEATURES                                        │
    └─────────────────────────────────────────────────┘
```

FIG. 3

Calcium Correspondence between Week 0 and Week 96
(Left)    (Right)

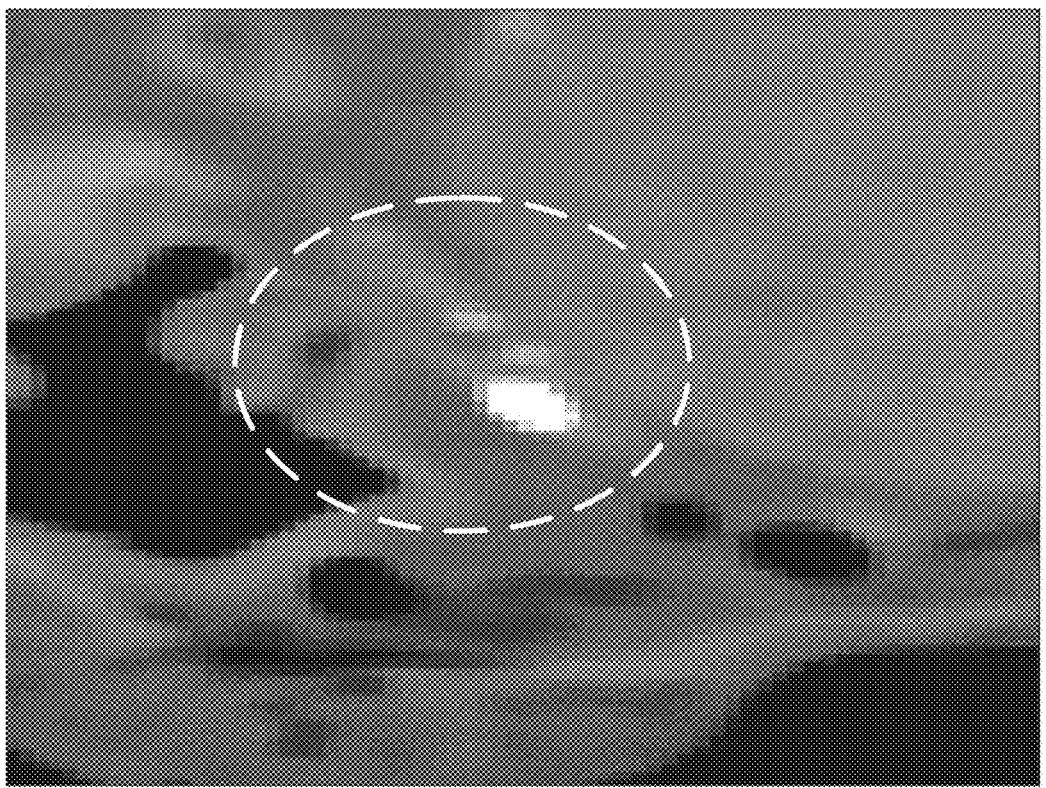
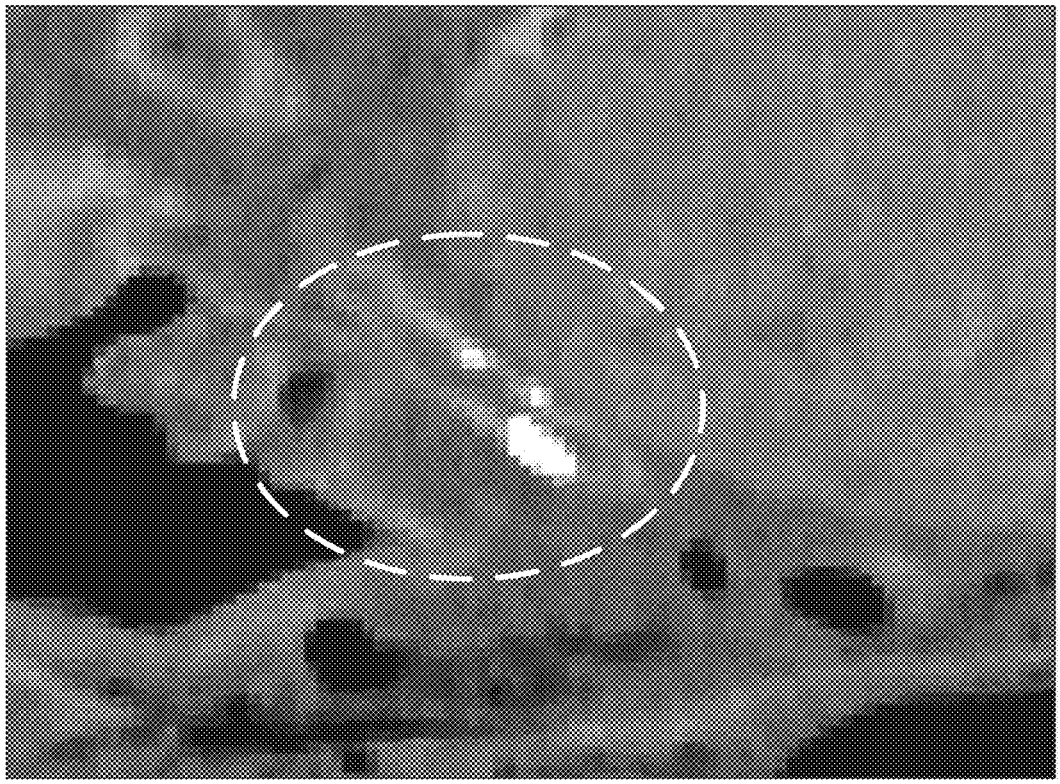
FIG. 10

ASSESSMENT OF ARTERIAL CALCIFICATIONS

CROSS REFERENCE TO RELATED APPLICATIONS

This application claims the benefit of U.S. Provisional Patent Application No. 62/808,444 filed Feb. 21, 2019, entitled "ASSESSMENT OF ARTERIAL CALCIFICATIONS", the contents of which are herein incorporated by reference in their entirety.

BACKGROUND

Coronary Artery Calcium (CAC) imaging proves the presence of coronary artery disease with near 100% specificity and predicts the risk of serious coronary events. A great number of studies have shown that CT calcium score (typically Agatston) aids risk prediction and is more predictive than any other single biomarker, including lipids. In a review of studies between 2008 and 2016, adding CAC score to traditional risk factors always improved AUCs (Area Under (Receiver Operating Characteristic) Curve) for risk prediction. An American College of Cardiology (ACC)/American Heart Association (AHA) group recommends the pooled cohort equation (PCE), much improved over Framingham, for estimating atherosclerotic cardiovascular disease (ASCVD) risk, and suggested Agatston >300 for revision of risk. A 2016 report found CAC score was the best among other nontraditional risk factors (ankle-brachial index, high-sensitivity C-reactive protein, and family history) for improving ASCVD risk from a "calibrated" PCE (Defined ASCVD events do not include peripheral artery disease, heart failure, revascularization, and other atherosclerosis-related, life-altering events). Calcium score can play a role for high risk groups having metabolic syndrome, HIV, cancer, and family history. Importantly, as compared to a 10-year risk (which are ill understood and easily "debunked" by a patient), showing patients images of disease improves adherence to statins and weight loss. Since there is 50% statin adherence at 1 year and 25%-40% at 5 years, improvements would increase quality-adjusted-life years and reduce costs.

Many have found whole-heart CT Agatston calcium score progression over time to be a valuable biomarker. Calcium progression of >300 was associated with high hazard ratios as compared to without progression. Progression was associated with higher risk of all-cause mortality among patients having low risk from traditional factors. One report showed increased risk with increasing whole heart calcium progression as measured on outdated electron beam CT technology, but concluded that data did not support its use as compared to using the second scan alone. Calcification progression has been studied for disease progression in diabetes; fatty liver disease; race; HIV; neighborhood (healthy food resources); hemodialysis; bariatric surgery; atrial fibrillation; vitamin K therapy in hemodialysis; periodontal disease in diabetes; rheumatoid arthritis; anti-human heat shock protein-60 and interleukin-2; obstructive sleep apnea; changes in traditional risk factors; and exercise. One report indicates that a particular high dose, long-term statin therapy accelerated CAC. Two groups addressed the issue of whether increasing calcification is disease progression or stabilization and argue for second-generation analysis.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 2 illustrates a flow diagram of an example method/set of operations that can be performed by one or more processors to perform a serial assessment of arterial calcification over two or more time-points based on CT image volumes for those time points, according to various aspects discussed herein.

FIG. 3 illustrates a flow diagram of an example method/set of operations that can be performed by one or more processors to train a ML and/or DL model to determine a risk of adverse clinical outcome(s) based on a CT arterial calcium image volume, according to various aspects discussed herein.

FIG. 10 illustrates a pair of example images showing high resolution and normal resolution cadaver image volume showing partial volume blur, in connection with various aspects discussed herein.

DETAILED DESCRIPTION

Figure 1:
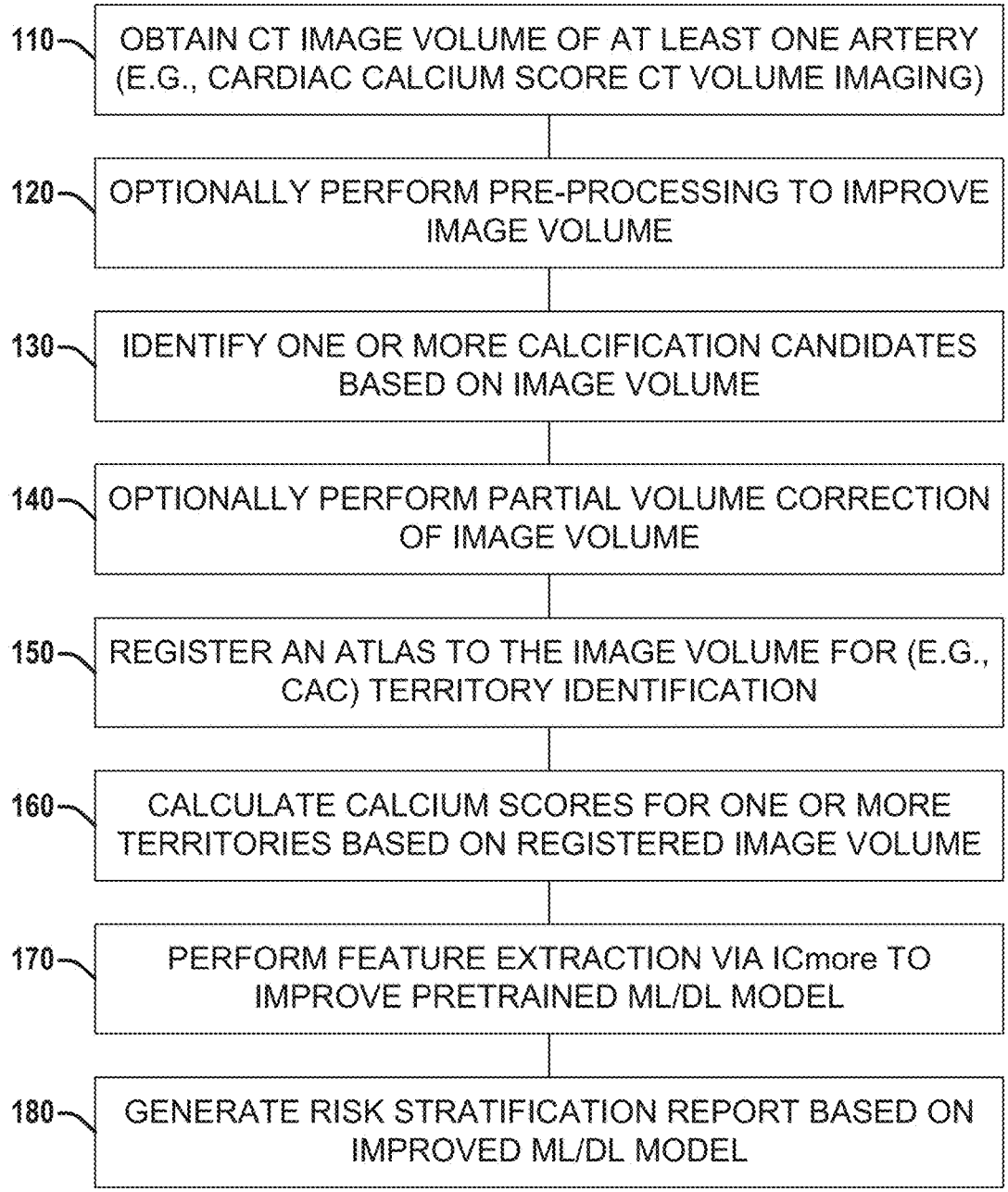
FIG. 1 illustrates a flow diagram of an example method/set of operations that can be performed by one or more processors to perform a single assessment of arterial calcification at one time-point based on a CT image volume, according to various aspects discussed herein.

Various embodiments discussed herein can comprise techniques that can facilitate analysis of calcifications seen with computed tomography (CT) imaging. Various embodiments can employ techniques discussed herein to enable one or more of a single assessment or a serial assessment over time of individual arterial calcifications observable in CT. Since the most common application of calcification analysis is in connection with coronary arteries, various example embodiments and use cases are described in terms of coronary artery calcification (CAC); however, embodiments and techniques discussed herein can be employed in connection with calcification of other arteries, as well.

CT coronary calcium imaging gives direct evidence of coronary artery disease in a reliable, cost-effective, non-invasive, contrast-agent-free fashion. In several large, long-term studies, CT calcium score has been shown to be an essential factor for predicting the risk of coronary heart disease, with a higher score giving increased 10-year risk. There are many studies of calcification progression over time that examine correlation with other biomarkers, response to drug therapy, effects of environmental factors, improvements to risk estimates, etc. To date, progression studies have used serial assessments of whole-heart Agatston score. From pathobiology and clinical observations, it is likely that progression of small, spotty calcifications will provide better evidence of disease progression than whole-heart Agatston, which is numerically dominated by large, potentially stable, calcifications. Accordingly, various embodiments can employ a new analysis paradigm discussed herein, which analyzes Individual Calcification measures including morphological features and progression/regression/formation changes over time (referred to herein as ICmore) measures. Additionally, various embodiments can employ an approach discussed herein for registering a patient's coronary calcifications over time so as to determine calcification correspondence. Various embodiments can analyze calcium change, also referred to herein as CaChange. Embodiments discussed herein can provide a variety of outputs, including traditional (e.g., mass score and Agatston) and non-traditional (e.g., length and distance to ostium) calcification measures, optionally with partial volume and/or deconvolution correction, which can improve precision and accuracy. As explained below, ICmore measures are expected to be highly predictive of disease progression, and will give physicians improved assessments of patient risk. For assessment of drug therapy, it is anticipated that ICmore measures will depend on time, treatment, and possibly inflammation; and will show more significant effects than whole heart Agatston score. Because CT is easy to use, non-invasive, and applicable to coronary artery disease, various embodiments discussed herein can be employed as a new, non-invasive, valuable research tool for assessing the role of genes, environment, life style, and drug treatments on coronary artery disease. By imaging persons at intervals over time (e.g., every N months or years, such as a 5-year interval, etc.) and analyzing risk according to techniques discussed herein, it can be possible for physicians to identify those patients of very high risk for disease. Additionally, although various example embodiments and use cases discussed herein involve assessing coronary arteries, techniques discussed herein can be applied equally well to any arteries in the body.

In various embodiments, second-generation progression and characterization (density, shape, location, etc.) techniques discussed herein can be employed on individual calcifications, which is believed to be more sensitive to new lesion development than whole-heart Agatston based on several observations. (1) The calcification process proceeds from micro-calcifications, not visible in clinical CT, within lipid pools; to coalesced larger masses to form speckled and fragmented calcifications; and finally to calcified plates and nodules. This suggests that formation and changes in characteristics of calcifications over time, particularly in early stages, will be an indicator of newer lesion activity. (2) Micro-calcifications have been identified as potentially contributing to plaque instability, hinting that formation of new calcifications will be a measure of new, vulnerable lesion formation. (3) Autopsy and intravascular imaging studies reported that "spotty" calcifications, rather than large calcifications, are seen in plaques that have ruptured. Although some "spotty" calcifications in pathology are under detection limits of conventional CT, this observation suggests it will be important to track small, low-density calcifications. At a larger scale, spotty calcifications in CT have been associated with risk of acute coronary syndrome. (4) Other calcification morphologies, including diffuse, shell-like, and nodular, have been deemed important for identifying the presence of stenotic and non-calcified lesions. (5) Whole heart, calcification "density," determined circuitously from Agatston, was significantly associated with risk. (6) There is emerging evidence that regional calcification is important. In pathology samples, one group remarked that they never found a ruptured lesion in a coronary artery without a calcification, suggesting the importance of territory analysis. Numbers of arteries with calcifications and a "diffusivity index" assessing calcification outside the main culprit lesion improved risk prediction as compared to whole-heart Agatston.

Various embodiments can employ one or more techniques discussed herein, which provide several advantages over existing techniques. (1) Embodiments discussed herein can shift the current CAC research paradigm by focusing on progression/regression/formation of individual calcifications rather than whole heart Agatston, the current "standard." From pathobiology and clinical observations, it is likely that progression of small, newer calcifications (e.g., as analyzed by embodiments discussed herein) will provide better evidence of disease progression than whole-heart Agatston, which is numerically dominated by large, potentially stable, calcifications. (2) Various embodiments can employ an image registration approach discussed herein that can employ an iterative closest point with matching of calcification attributes in a high dimension space. (3) Various embodiments can employ an analysis paradigm that can involve analyzing Individual Calcification measures including morphological features and progression/regression/formation changes over time (ICmore) measures. (4) Various embodiments can employ techniques discussed herein to correct partial volume error in ICmore measures, including mass score.

Techniques discussed herein can be employed by various embodiments to facilitate one or more of single assessment and/or serial assessment of arterial calcification (e.g., coronary artery calcification). These techniques comprise techniques that facilitate: (1) Calcification registration and visualization; (2) improving the precision of assessment (e.g., as assessed via repeatability), including via deconvolution, partial volume correction, and super-resolution using deep learning (DL); (3) ICmore single time-point and serial assessments; and (4) Machine learning (ML) to improve cardiovascular risk assessments and/or effects of one or more of drugs, genes, environment, or disease confounds. Each of these techniques are discussed in greater detail below, along with example application of these techniques to a use case involving CAC, although techniques discussed herein also can be employed in connection with calcification of other arteries.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Referring to FIG. 1, illustrated is a flow diagram of an example method/set of operations 100 that can be performed by one or more processors to perform a single assessment of arterial calcification at one time-point based on a CT image volume, according to various aspects discussed herein. Processor(s) can include any combination of general-purpose processors and dedicated processors (e.g., graphics processors, application processors, etc.). The one or more processors can be coupled with and/or can include memory or storage and can be configured to execute instructions stored in the memory or storage to enable various apparatus, applications, or operating systems to perform the operations. The memory or storage devices may include main memory, disk storage, or any suitable combination thereof. The memory or storage devices can comprise—but is not limited to—any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The set of operations 100 can comprise, at 110, obtaining a CT image volume of one or more arteries of a patient. In various embodiments and in the example use case discussed below, the CT image volume of one or more arteries can comprise a cardiac CT image volume such as obtained via cardiac calcium score CT volume imaging. In other embodiments, a CT image volume of other arteries can be obtained. The image volume can be obtained via a system and/or apparatus implementing the set of operations 100, or can be obtained from a separate medical imaging system 100. Additionally, the image volume can be accessed contemporaneously with or at any point prior to performing the set of operations 100.

The set of operations 100 can further comprise, at 120, optionally performing pre-processing on the CT image volume obtained at 110 to improve the CT image volume. The pre-processing can comprise one or more of the techniques discussed herein, such as partial volume correction, deconvolution, or generating a super-resolution CT image volume based on the obtained CT image volume.

The set of operations 100 can further comprise, at 130, identifying one or more calcification candidates based on the CT image volume, which can be one or more areas on the one or more arteries that have or could have calcification as determined from the CT image volume (e.g., N (e.g., 3) connected voxels>X (e.g., 130) HU (Hounsfeld Units), etc.).

The set of operations 100 can further comprise, at 140, optionally performing partial volume correction of the CT image volume, such as discussed in greater detail below, to correct volume estimates of the calcification candidates identified at 130.

The set of operations 100 can further comprise, at 150, registering one or more atlases to the CT image volume for an anatomical region of the one or more arteries (e.g., coronary arteries), in order to identify one or more relevant territories (e.g., relevant to coronary artery calcification), as discussed in greater detail below.

The set of operations 100 can further comprise, at 160, calculating a calcium score for the one or more relevant territories based on the registered CT image volume. The territory calcium score can be computed for that territory in a manner similar to a whole heart Agatston score, but specific to that territory.

The set of operations 100 can further comprise, at 170, performing feature extraction via ICmore to improve a pretrained ML (machine learning) and/or DL (deep learning) model.

The set of operations 100 can further comprise, at 180, generating a risk stratification report (e.g., predicting a risk of one or more outcomes (e.g., adverse events, etc.), etc.) based on the improved ML/DL model.

Referring to FIG. 2, illustrated is a flow diagram of an example method/set of operations 200 that can be performed by one or more processors to perform a serial assessment of arterial calcification over two or more time-points based on CT image volumes for those time points, according to various aspects discussed herein.

The set of operations 200 can comprise, at 210, obtaining two or more CT image volumes of one or more arteries (e.g., coronary arteries) of a patient at each of two or more different time points (e.g., separated by some number of weeks, months, years, etc.). The CT image volumes can be obtained via a system and/or apparatus implementing the set of operations 200, or can be obtained from a separate medical imaging system 200. Additionally, the image volumes can be accessed contemporaneously with or at any point prior to performing the set of operations 200.

The set of operations 200 can further comprise, at 220, calculating, for each CT image volume, a territory calcium score for one or more identified territories (e.g., identified for that CT image volume and/or at least one other CT image volume), based on techniques discussed below and in connection with FIG. 1.

The set of operations 200 can further comprise, at 230, extracting, for each CT image volume, one or more ICmore features in each calcified region of the one or more identified territories.

The set of operations 200 can further comprise, at 240, performing registration of the CT image volumes from each time point to each other (e.g., registering each CT image volume from an earlier time point to the CT image volume of the latest time point as a reference, etc.).

The set of operations 200 can further comprise, at 250, analyzing changes in the extracted ICmore features over time from the different CT image volume, for example, via a pretrained ML and/or DL model.

The set of operations 200 can further comprise, at 260, predicting a risk of one or more adverse events (e.g., adverse cardiovascular events) based on the analyzed changes in the extracted ICmore features over time, for example, as determined via the pretrained ML and/or DL model.

Referring to FIG. 3, illustrated is a flow diagram of an example method/set of operations 300 that can be performed by one or more processors to train a ML and/or DL model to determine a risk of adverse clinical outcome(s) based on CT arterial calcium imaging, according to various aspects discussed herein.

The set of operations 300 can comprise, at 310, obtaining a CT image volume of one or more arteries of a patient or subject of a training set. In various embodiments and in the example use case discussed below, the CT image volume of one or more arteries can comprise a cardiac CT image volume such as obtained via cardiac calcium score CT volume imaging. In other embodiments, a CT image volume of other arteries can be obtained. The image volume can be obtained via a system and/or apparatus implementing the set of operations 300, or can be obtained from a separate medical imaging system 300. Additionally, the image volume can be accessed contemporaneously with or at any point prior to performing the set of operations 300.

The set of operations 300 can further comprise, at 320, obtaining a clinical outcome (e.g., adverse cardiovascular event, lack thereof, etc.) associated with the patient that was the subject of the CT image volume.

The set of operations 300 can further comprise, at 330, optionally performing pre-processing on the CT image volume obtained at 310 to improve the CT image volume. The pre-processing can comprise one or more of the techniques discussed herein.

The set of operations 300 can further comprise, at 340, identifying one or more calcification candidate regions based on the CT image volume.

The set of operations 300 can further comprise, at 350, extracting one or more ICmore features in the one or more calcification candidate regions.

The set of operations 300 can further comprise, at 360, training a ML (Machine Learning) and/or DL (Deep Learning) model based on the extracted one or more ICmore features and the clinical outcome.

The set of operations 300 can be repeated for each patient or subject of the training set.

Additional aspects and embodiments are discussed below in connection with the following example use case.

Example Use Case: Assessment of Arterial Calcifications

The following discussion provides example embodiments in connection with an example use case involving assessment of arterial calcifications via techniques discussed herein. These techniques comprise: (A) Calcification registration and visualization; (B) Methods to improve precision (as assessed via repeatability), including deconvolution, partial volume correction, and super-resolution using deep learning; (C) ICmore single-time-point and serial assessments; and (D) Machine learning to improve cardiovascular risk assessments and effects of drugs, genes, drugs, genes, environment, and disease confounds.

Each of techniques (A)-(D) are described in greater detail below. Although this use case describes these techniques in the context of CT coronary artery calcifications, the techniques are applicable to other calcifications in other arteries.

A. Calcification Registration and Visualization

Various embodiments (e.g., software and/or hardware, etc.) can detect, link, and enable visualization of calcifications in a single CT image volume and/or individual, corresponding calcifications in serial CT image volumes. Volume mask(s) can be created for one or more major coronary territories via registration to atlases and aggressively detect potential coronary calcifications. To identify corresponding calcifications as compared to a previous reference volume, gray-scale registration can be employed, followed by a novel application of the iterative closest point algorithm (ICP) that matches location as well as one or more calcification attributes, for example, mass score. Visualization and/or editing tools can be employed for serial measurements.

Algorithm details. To identify coronary artery territories, a heart atlas can be registered to a new CT image volume of the heart, to identify one or more regions appropriate for coronary calcifications. Within appropriate regions, an aggressive approach can be applied to detect calcifications. For example, one criterion that can be employed for identifying coronary calcifications can be 3 connected voxels>130 HU (Hounsfield Units). This is more aggressive than the criterion used in existing techniques, which was 6 voxels. Other choices are possible (e.g., greater or lesser than 3 pixels, greater or lesser than 130 HU). Additionally, in some embodiments, serial heart image volumes (e.g., CT image volumes of the same heart taken at two or more time points, e.g., each separated by approximately the same number of years, months, weeks, etc.) can be registered to each other. Finally, this portion describes techniques associated with ICmore measures. Some results are shown regarding registration (e.g., in connection with FIGS. 6-8, discussed in greater detail above) and visualization (e.g., in connection with FIGS. 4-8, discussed in greater detail above). Details of the algorithm and associated techniques are discussed below.

Registration to atlas and spatial mapping of labels. In various embodiments, volume-to-atlas registration can be performed for a CT image volume of a heart (also referred to herein as the CT volume or heart volume). The registration techniques can comprise techniques to prepare the image volume for registration, for example, cropping and down sampling, as well as registering the new CT volume (e.g., as reference) with each of a plurality of (e.g., 16) atlas (e.g., floating) volumes and choose the best one, for example, as determined from grayscale normalized-cross-correlation. As one example, a normalized cross correlation registration can be used, with Affine followed by B-spline. All volumes can be aligned (e.g., anterior-posterior, ventral-dorsal) prior to registration. After identifying the best match, non-rigid registration can be employed at full resolution to map the atlas to the non-contrast CT volume. Atlas labels can include ventricles, atria, and territories (e.g., LAD (Left Anterior Descending), LCX (Left Circumflex), and RCA (Right Coronary Artery), etc.).

Registration of serial data to identify calcification correspondence. In embodiments associated with serial CT imaging, CT volumes acquired at different time points can be co-registered, with the last volume as reference (because it likely contains the most calcifications) and earlier volumes as floating (in some embodiments, registration can be to the volume determined to have the most calcifications, etc.). Initially, gray-scale normalized-cross-correlation rigid body (translation and rotation) registration can be used to register a reference and floating volume. From this, roughly registered hearts with residual error can be obtained, such as images 400 and 410 of FIG. 4, discussed below. After rough registration, an iterative closest point (ICP) algorithm with rigid body transformation to align calcifications can be used. However, rather than just using two 3D point clouds, such as in existing techniques, various embodiments discussed herein can assign one or more morphological characteristics (e.g. center, divergence, max HU, etc.) to each calcification, and can perform ICP in a higher dimensional space so that calcifications of similar shape and size will match. This increases robustness as compared to simpler algorithms that can be trapped in local minima. ICP works with different numbers of points in reference and floating volumes, giving results robust to new and lost calcifications.

Visualization and editing. Calcifications tend to be small and surface renderings are irregular due to partial volumes and noise. Accordingly, various embodiments can create volume visualizations with an optimized opacity function and show calcifications superimposed or in separate windows, with or without CT data. Linked slicer operations can be employed to facilitate examination of registered CT image data for image evidence of an early calcification. Additionally, various embodiments can comprise an editing tool for adding, removing, splitting, and merging calcifications, as well as changing correspondence.

Potential modifications. Optionally, in various embodiments, registration can be improved by adding other/additional morphological features for ICP registration. Additionally, for registering a new CT volume to an atlas, some embodiments can apply one or more of multi-resolution image registration, a pipeline of rigid body to B-spline registration, tune spatial regularization, registration to more atlas volumes, etc.

FIGS. 4-8 relate to aspects discussed in this section.

Figure 4:
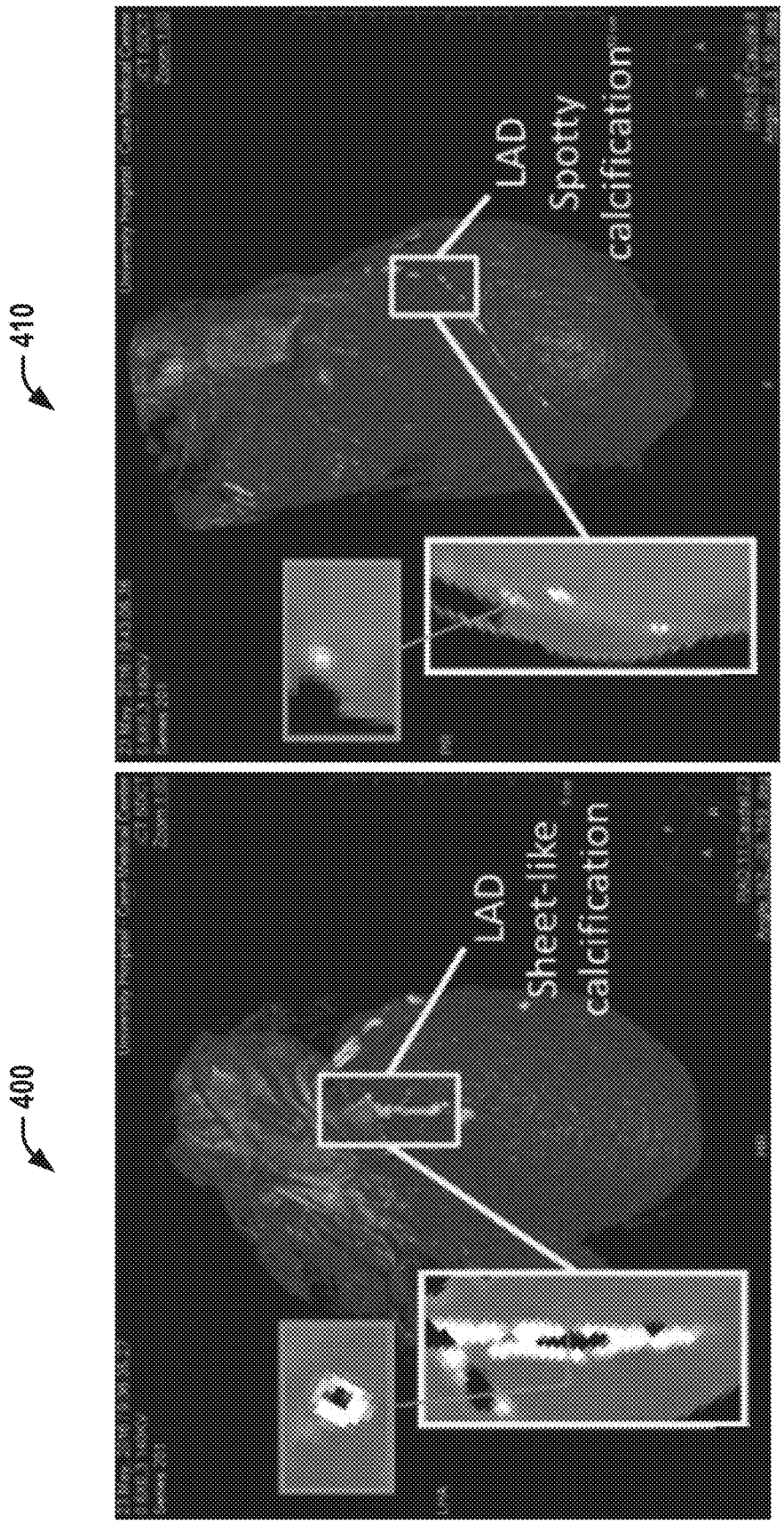
FIG. 4 illustrates a pair of example images showing a roughly registered CT heart image volume, with sheet-like calcification in the left image and spotty calcification in the right image, in connection with aspects discussed herein.

Referring to FIG. 4, illustrated is a pair of example images 400 and 410 showing a roughly registered CT heart image volume, with sheet-like calcification in the left image 400 and spotty calcification in the right image 410, in connection with aspects discussed herein. The sheet calcification in image 400 encircles the vessel, as shown via the inset views. Spotty calcification, such as that of image 410, is associated with more rapid progression and greater risk of major adverse cardiac events.

Figure 5:
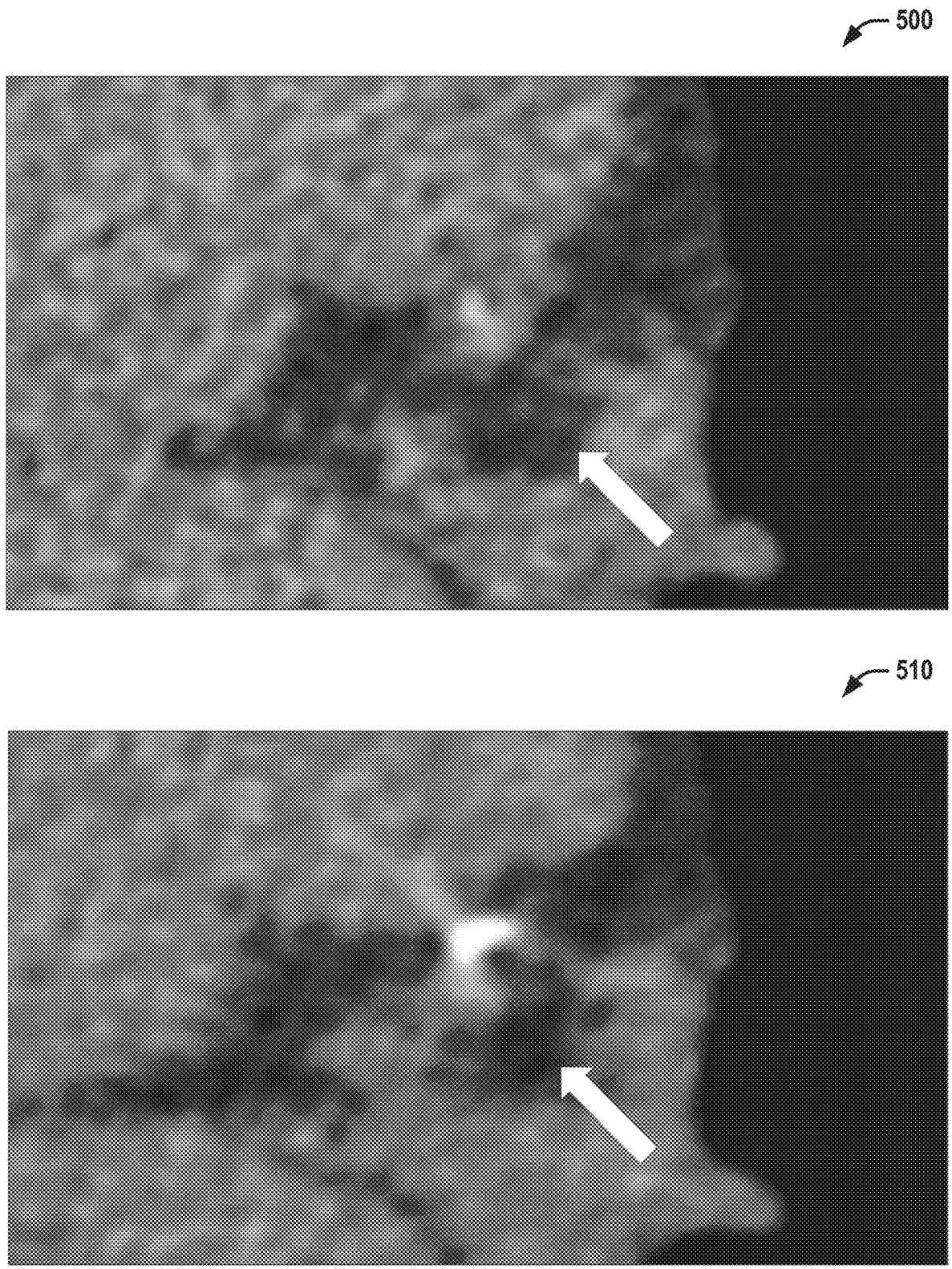
FIG. 5 illustrates a pair of example images showing formation of LAD calcified plaque, in connection with aspects discussed herein.

Referring to FIG. 5, illustrated is a pair of example images 500 and 510 showing formation of LAD calcified plaque, in connection with aspects discussed herein. Clearly detectable plaque in image 510 (taken at 96 weeks) can be seen (but not detected via standard practice) in image 500 (taken at 48 weeks). An image volume taken at 0 weeks (not shown) did not show LAD calcified plaque.

Figure 6:
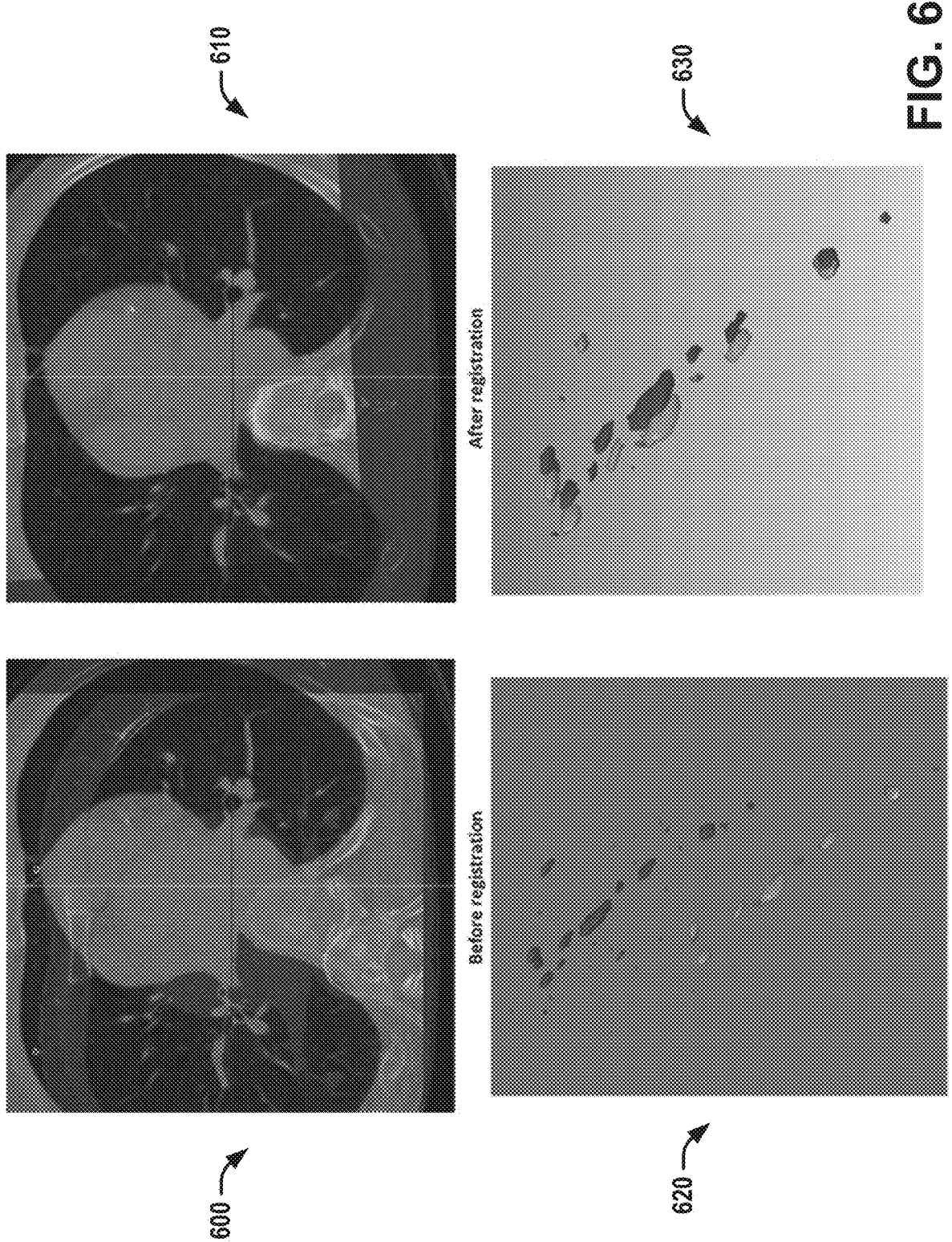
FIG. 6 illustrates example images showing a cardiac CT image volume at different time points before and after registration, along with corresponding calcification at different time points before and after registration, in connection with aspects discussed herein.

Referring to FIG. 6, illustrated are example images showing cardiac CT image volumes at different time points before (600) and after (610) registration, along with corresponding calcification at different time points before (620) and after (630) registration, in connection with aspects discussed herein. Image 600 shows an axial CT image volume at weeks 0 and 96 before rigid heart registration, and image 610 shows the same image volume after registration. Similarly, image 620 shows surface renderings of calcifications at week 0 (light gray) and week 96 (dark gray) before registration, while image 630 shows the same surface renderings after registration. Once registered, correspondence between plaques can be established for assessment of plaque progression, regression, and formation.

Figure 7:
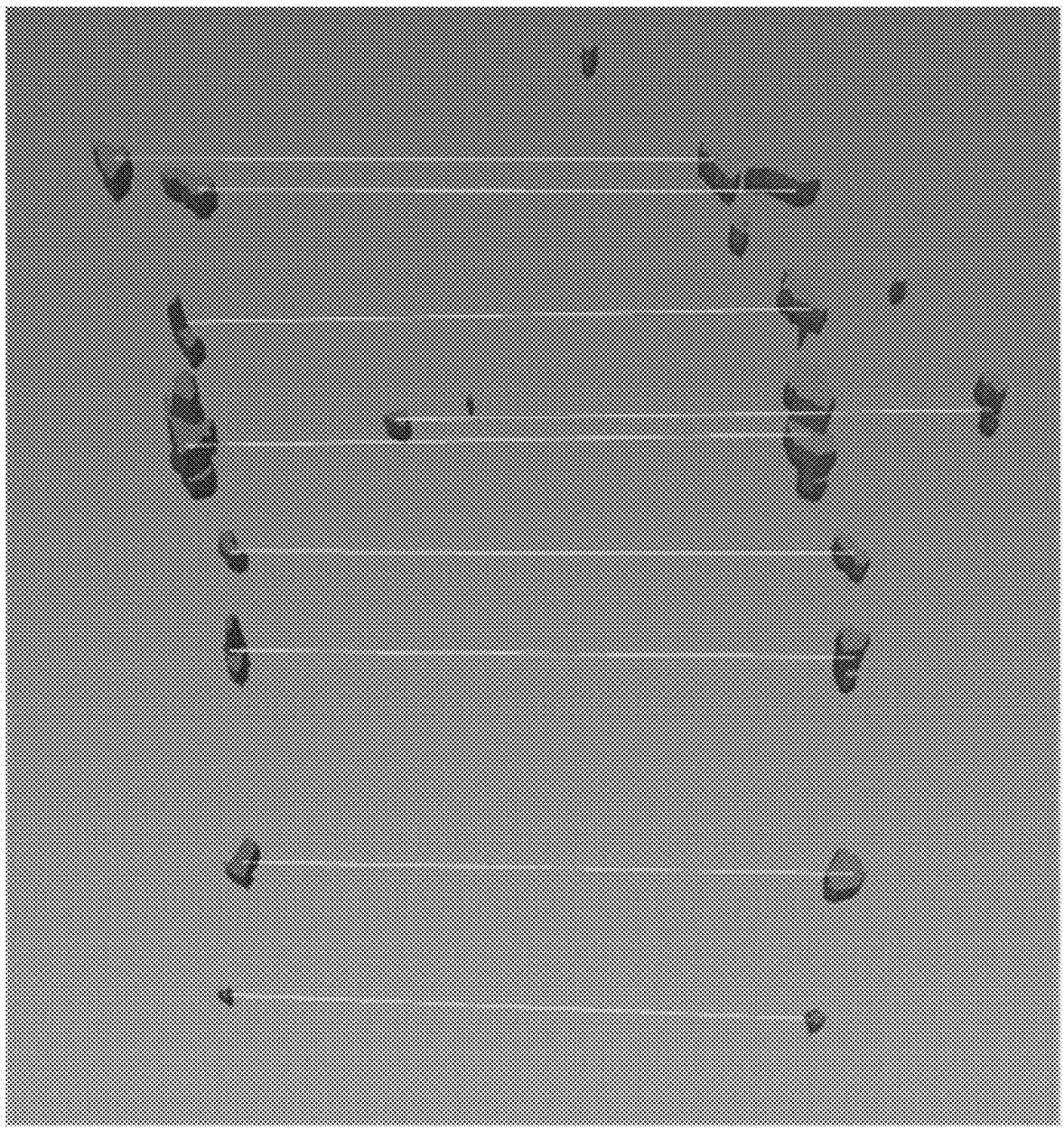
FIG. 7 illustrates a diagram showing an example of corresponding calcifications at week 0 and week 96, in connection with various aspects discussed herein.
Figure 8:
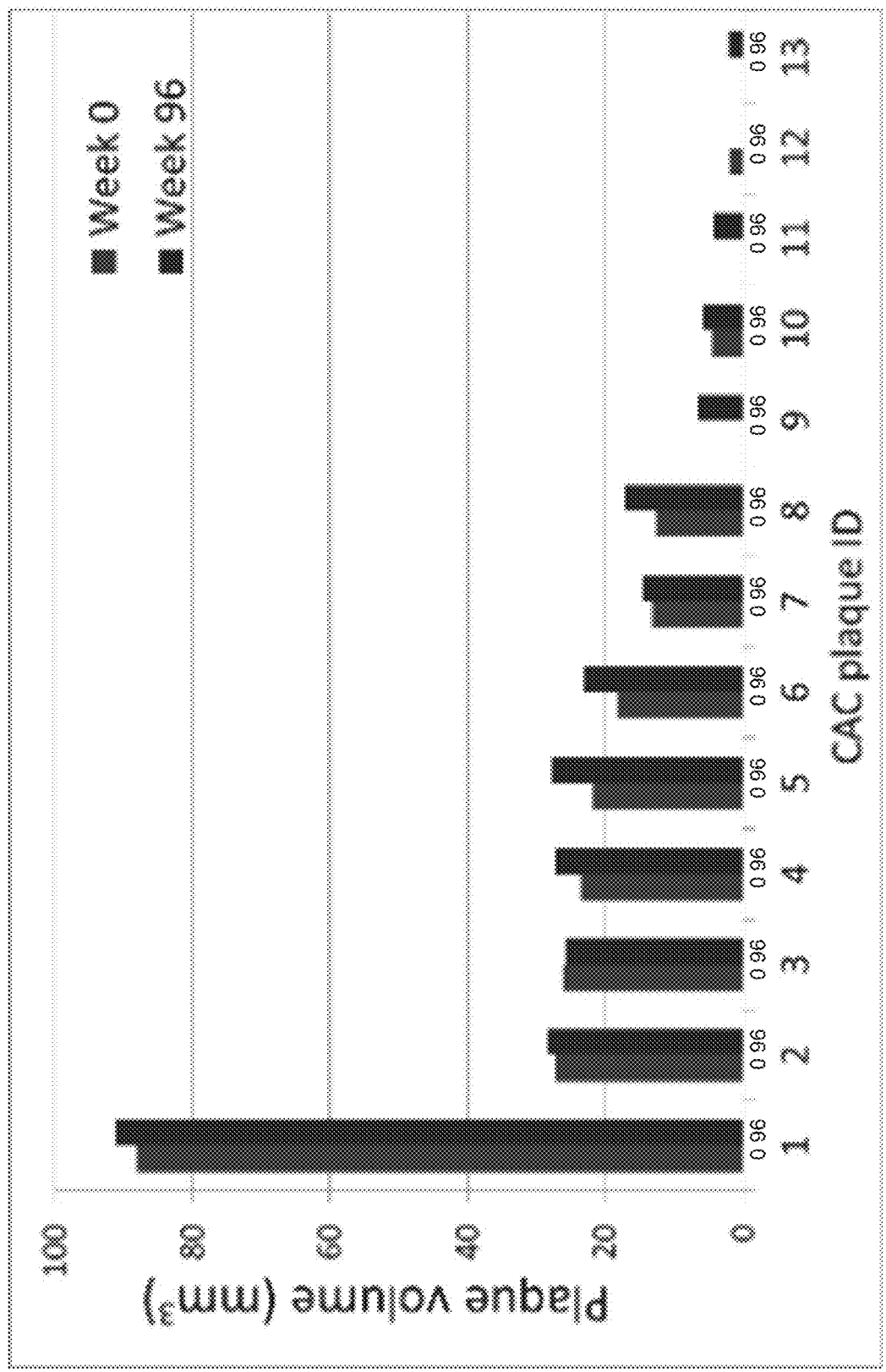
FIG. 8 illustrates a graph showing change in calcium score (e.g., plaque volume) for corresponding calcifications shown in FIG. 7 at week 0 and week 96, in connection with various aspects discussed herein.

Referring to FIG. 7, illustrated is a diagram showing an example of corresponding calcifications at week 0 and week 96, in connection with various aspects discussed herein. Referring to FIG. 8, illustrated is a graph showing change in calcium score (e.g., plaque volume) for corresponding calcifications shown in FIG. 7 at week 0 and week 96, in connection with various aspects discussed herein. As can be seen in FIGS. 7-8, nearly all of the calcifications progressed in size, three new calcifications (#9, #11, and #13) were formed, and one calcification from week 0 (#12) was not detected at week 96. Similar analyses can be conducted for other measures discussed herein.

Images of diseased cadaver hearts in FIG. 4 show sheet and spotty calcifications, morphologies of interest for determining patient vulnerability. The gray-scale registration method results in closely aligned calcifications at 0 and 96 weeks shown in FIG. 6 enables analysis of individual calcification progression as measured with a volume score, such as shown in FIGS. 7-8. Registration (e.g., as shown in connection with FIG. 5) also facilitates determination of calcification formation.

B. Methods to Improve Precision (Repeatability), Including Deconvolution, Partial Volume Correction, and Super-Resolution Using Deep Learning In coronary calcium score image acquisitions, thick image slices are typically used (e.g., on the Philips systems, voxel sizes of 0.49 mm×0.49 mm×2.5 mm are often used). As a result of thick slice imaging, the orientation of an irregular calcification with respect to the CT "reconstruction grid" can confound numerical assessments. In various embodiments, one or more techniques discussed herein can be employed to effectively improve resolution and reduce the variability due to orientation of a calcification within the scanner, making measurements more precise (repeatable). These techniques comprise the following approaches, which are discussed below: partial volume correction, deconvolution, and super-resolution using deep learning.

Figure 11:
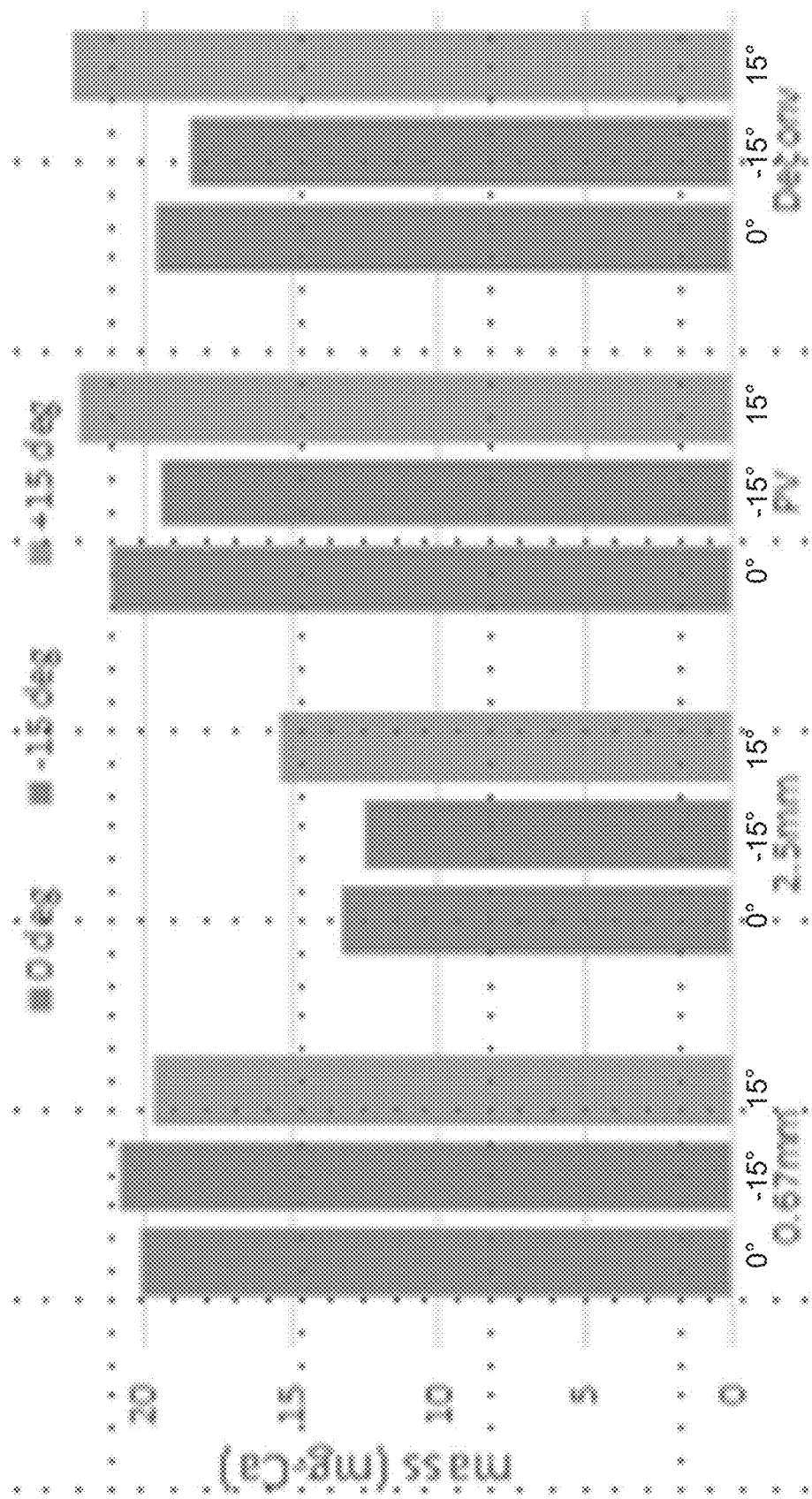
FIG. 11 illustrates a graph showing mass scores from scanning at 0°, −15°, and 15° at high resolution, compared to normal resolution, normal resolution after partial volume (PV) correction, and normal resolution after deconvolution, in connection with various aspects discussed herein.
Figure 12:
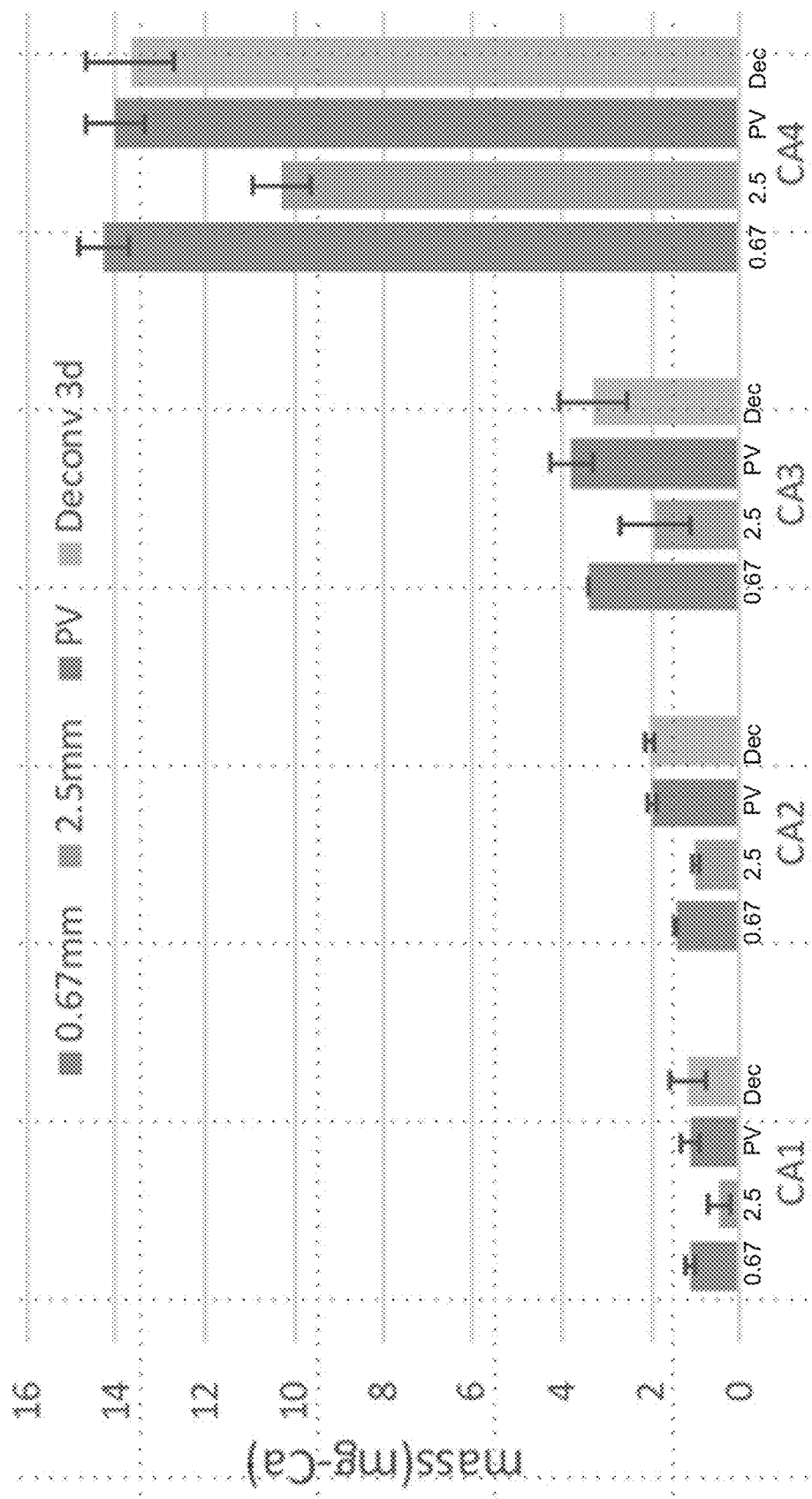
FIG. 12 illustrates a graph showing mass scores across 4 calcifications (CA1-CA4) in a cadaver heart at high resolution, normal resolution, normal resolution with partial volume correction and normal volume with 3D deconvolution, in connection with various aspects discussed herein.

Partial volume correction. Various embodiments can employ a partial volume correction algorithm designed in connection with various embodiments (e.g., as discussed in connection with FIG. 9), which gives improved accuracy and reproducibility of mass score, as can be seen in FIGS. 10-12. To account for partial volumes in mass score, each calcification volume ($V_C$) can be used to seed a 3D region growth (26-n or 6-n) to a threshold of background+20 HU (in other embodiments, a greater or lesser threshold can be employed), giving a partial volume ($V_P$) region. To obtain the total HU attributable to calcium, the voxel values can be summed in $V_C$, and the difference between the voxel value and background can be summed in $V_P$. HU can be converted to mg-Ca using standard calibration techniques. To correct volume estimates, for each voxel within $V_P$, HU values in the 3 (or other greater or lesser number of) nearest voxels in $V_C$ can be averaged to assess the local full calcification value, $HU_C$. The voxel value of interest can be a weighted sum, $HU=\alpha(HU_C)+(1-\alpha)(HU_{BKG})$, where $\alpha$ is the volume fraction occupied by calcification. This equation can be solved for $\alpha$ and the partial volume contributions can be added up. In various embodiments, when appropriate, other CAC measures can be corrected similarly.

3D deconvolution of calcifications. To perform deconvolution, a model for CT system degradation can be assumed. In various embodiments, the CT system can be assumed to be linear and spatially invariant, thus the output blurred image with additive noise is given by equation (1):

$$I(x, y, z) = \int\int\int f(x', y', z')h(x-x', y-y', z-z')dx'dy'dz' + n(x, y, z) \qquad (1)$$
$$= f(x, y, z) * h(x, y, z) + n(x, y, z),$$

where I(x, y, z) is the measured image volume from the CT system, f(x, y, z) is the idealized input image, '*' denotes convolution, h(x,y,z) represents the 3D PSF, and n is additive noise. The 3D point spread function, PSF, can be measured using a phantom, such as one containing very small metal beads. Alternatively, the PSF can be assumed to be a 3D Gaussian distribution, with parameters estimated from a phantom with discrete objects or from a more general phantom or patient in an iterative solution.

In some embodiments, deconvolution can be performed via the Lucy-Richardson method, which is an iterative approach with the following characteristics. To estimate f, the method maximizes the likelihood of obtaining the output image data assuming Poisson noise statistics. The log likelihood is maximized in an iterative fashion. The PSF is assumed to be known, and the method constrains f to be non-zero. The method typically is reasonably fast and can be applied to three-dimensional problems. To reduce the effects of noise amplification, the method is modified to reduce noise. A damping coefficient is estimated from the noise in CT images and used. To reduce effects of noise even further, an anisotropic diffusion filter can be used in various embodiments.

In other embodiments, any of a variety of other approaches to deconvolution can be employed. Additionally, blind deconvolution can be employed whereby the PSF is estimated in addition to f. The iteratively obtained estimate of the PSF can be values stored in a 3D array which have been constrained in different ways (e.g., certain symmetries or non-negative values) or can be a 3D function.

Super-resolution from deep learning. Another technique that can be employed by various embodiments involves using a deep learning, generative adversarial network (GAN) to create super-resolution CT calcium score images from conventional, thick slice scans. For training, paired normal clinical resolution and high resolution volume scans can be used. These can be easily obtained with existing step and shoot multi-detector CT scan acquisition. The images can be simply reconstructed at both conventional thick slice and high resolution thin slice resolutions, giving perfectly paired data. After training, the network can create a high resolution scan volume from a low resolution clinical scan volume. Using the super-resolution volume, ICmore measures can be computed more accurately and precisely. GANs can be used to reduce noise in CT images, create super-resolution CT images, and create super-resolution MR images.

In various embodiments, different schemes can be used to create super-resolution image volumes from deep neural networks, such as the following example embodiment. This example embodiment can employ a modified version of a multi-level, densely connected super-resolution network (mDCSRN) with generative adversarial network (GAN)-guided training. By utilizing a densely connected network, the mDCSRN is extremely light-weight, and when trained with a Generative Adversarial Network (GAN), can create sharp and realistic-looking images. In various embodiments, existing network structures can be employed. This technique can employ a loss (or cost) function such as that given below in equation (2), where MSE is the mean square error between the actual and synthetic high resolution image volumes, lossCAC is the difference between the calcification mass score computed form the actual and synthetic high resolution images, lossGAN is the GAN discriminator loss, and the $\lambda$'s are empirically determined constants:

$$\text{loss}=\lambda 1\text{lossMSE}+\lambda 2\text{lossCAC}+\lambda 3\text{lossGAN} \qquad (1),$$

Using a properly optimized loss function, excellent results can be obtained.

FIGS. 9-14 relate to aspects discussed in this section.

Figure 9:
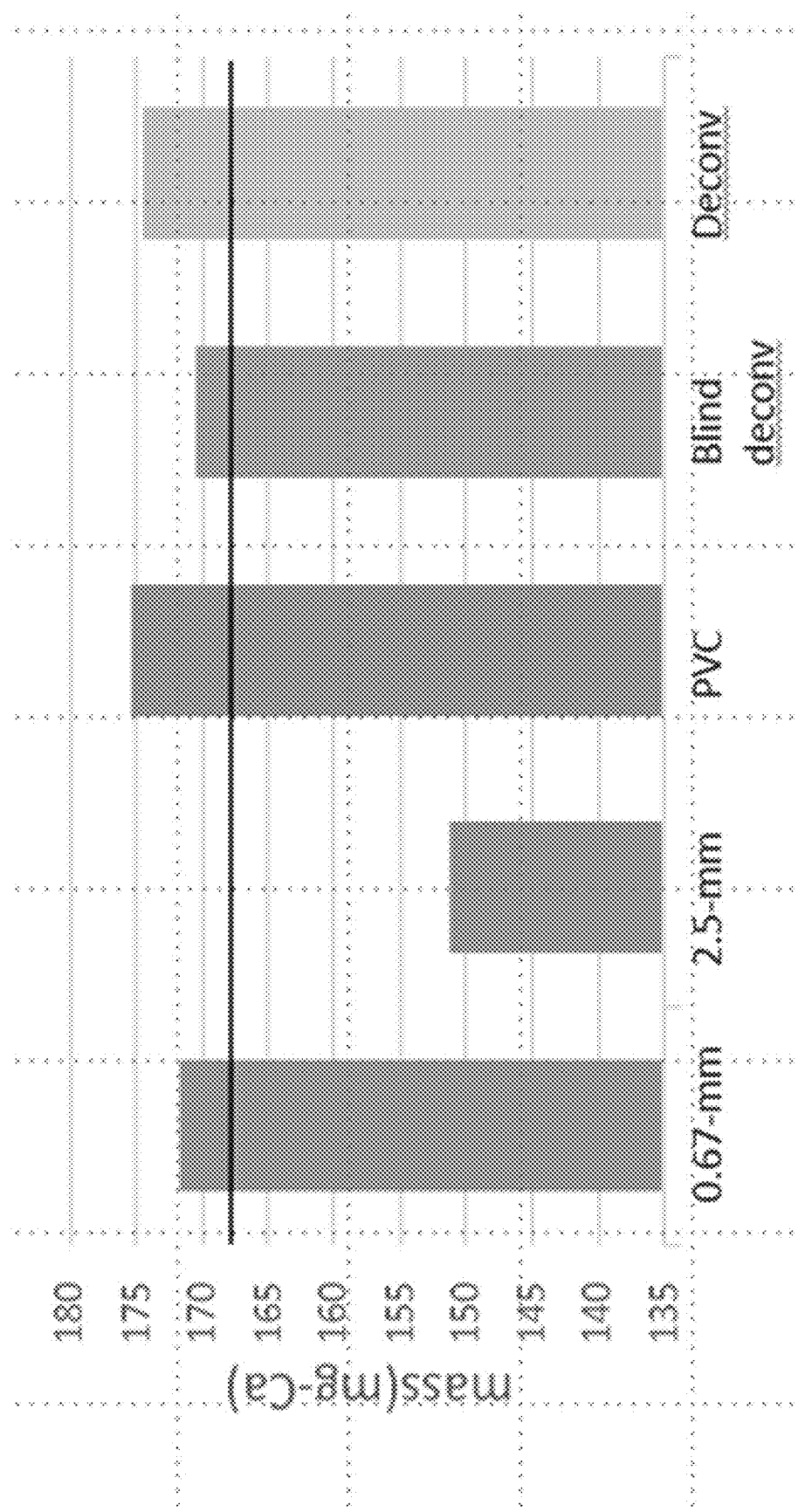
FIG. 9 illustrates a graph showing mass scores from a QRM calcification phantom obtained via various techniques, in connection with aspects discussed herein.

Referring to FIG. 9, illustrated is a graph showing mass scores from a QRM calcification phantom obtained via various techniques, in connection with aspects discussed herein. As can be seen in FIG. 9, mass scores can be improved with corrections towards the actual value (indicated via the horizontal line). The five mass scores shown in FIG. 9 are high resolution imaging (0.49 mm in plane, 0.67 mm thick), normal resolution imaging (2.5 mm thick) alone, normal resolution after partial volume correction (PVC), normal resolution after blind 3D deconvolution, and normal resolution after 3D deconvolution with estimated PSF (Point Spread Function). Blind deconvolution can iteratively improve an initial PSF.

FIGS. 10-12 illustrate ways in which correction techniques discussed herein can improve the accuracy and precision of mass score or other measures. Referring to FIG. 10, illustrated is a pair of example images showing a high resolution (1000) and a normal resolution (1010) cadaver image volume showing partial volume blur, in connection with various aspects discussed herein. Referring to FIG. 11, illustrated is a graph showing mass scores from scanning at 0°, −15°, and 15° at high resolution, compared to normal resolution, normal resolution after partial volume (PV) correction, and normal resolution after deconvolution, in connection with various aspects discussed herein. As can be seen in FIG. 11, after correction, the mass scores improve to match the more accurate, high resolution value. The precision was also improved with correction as COV (coefficient of variation) was 0.03, 0.11, 0.07, and 0.1, respectively. Referring to FIG. 12, illustrated is a graph showing mass scores across 4 calcifications (CA1-CA4) in a cadaver heart at high resolution, normal resolution, normal resolution with partial volume correction and normal volume with 3D deconvolution, in connection with various aspects discussed herein. After corrections on the normal resolution image volume, scores improved towards high resolution values. The average COV improved from 0.27 on normal scans to 0.1 and 0.17, following PVC and deconvolution, respectively.

Figure 13:
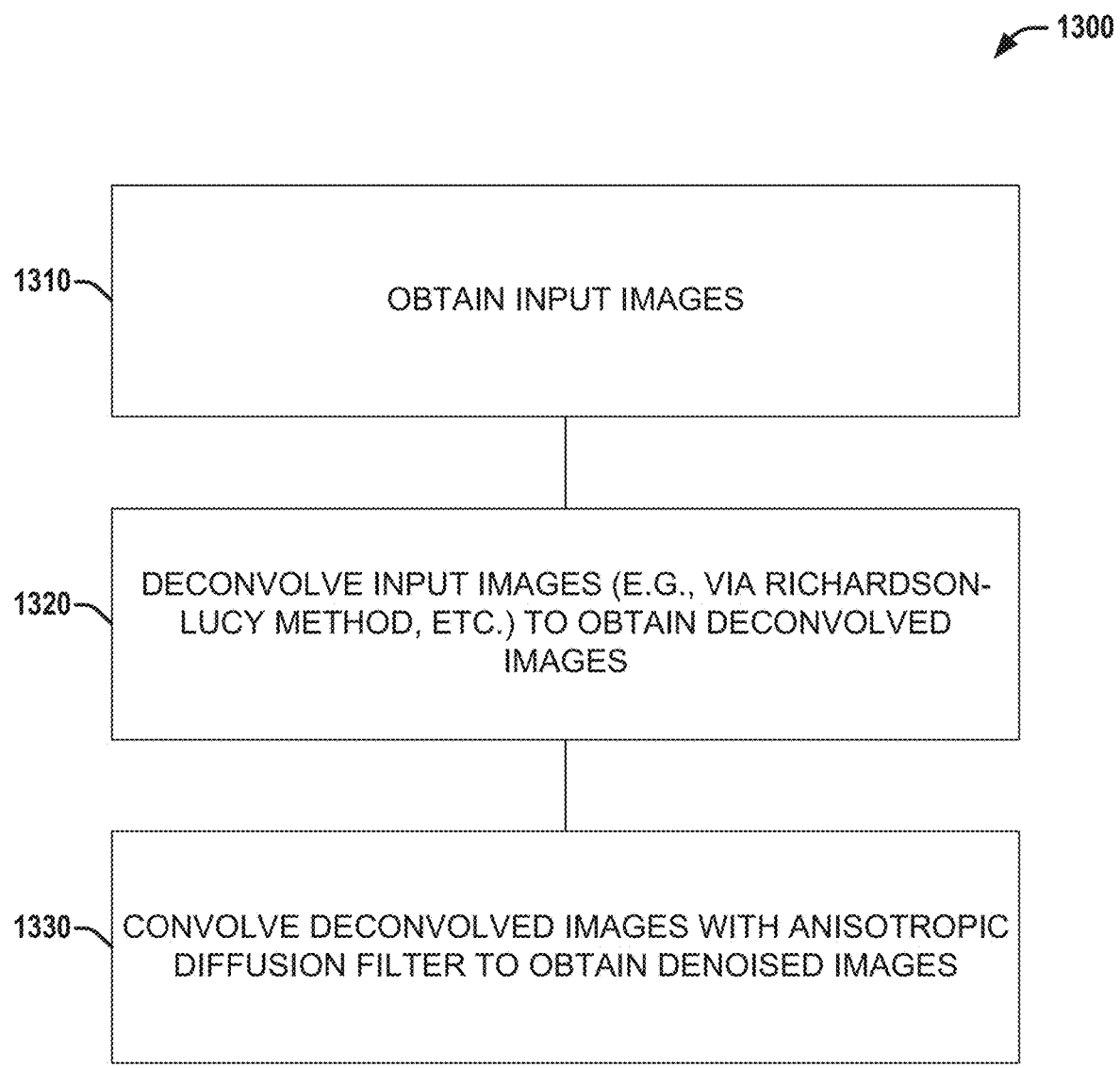
FIG. 13 illustrates a flow diagram showing an example method or set of operations that can be performed by one or more processors to improve calcification assessments via deconvolution techniques, according to various aspects discussed herein.

Referring to FIG. 13, illustrated is a flow diagram showing an example method or set of operations 1300 that can be performed by one or more processors to improve calcification assessments via deconvolution techniques, according to various aspects discussed herein.

The set of operations 1300 can comprise, at 1310, obtaining a set of input images (e.g., of a coronary CT image volume). The input images can be obtained via a system and/or apparatus implementing the set of operations 1300, or can be obtained from a separate medical imaging system. Additionally, the image volume can be accessed contemporaneously with or at any point prior to performing the set of operations 1300.

The set of operations 1300 can further comprise, at 1320, deconvolving the input images via any of a variety of techniques discussed herein (e.g., the Richardson-Lucy method, etc.) to obtain a set of deconvolved images.

The set of operations 100 can further comprise, at 130, convolving the set of deconvolved images with an anisotropic diffusion filter to obtain a set of denoised images.

Figure 14:
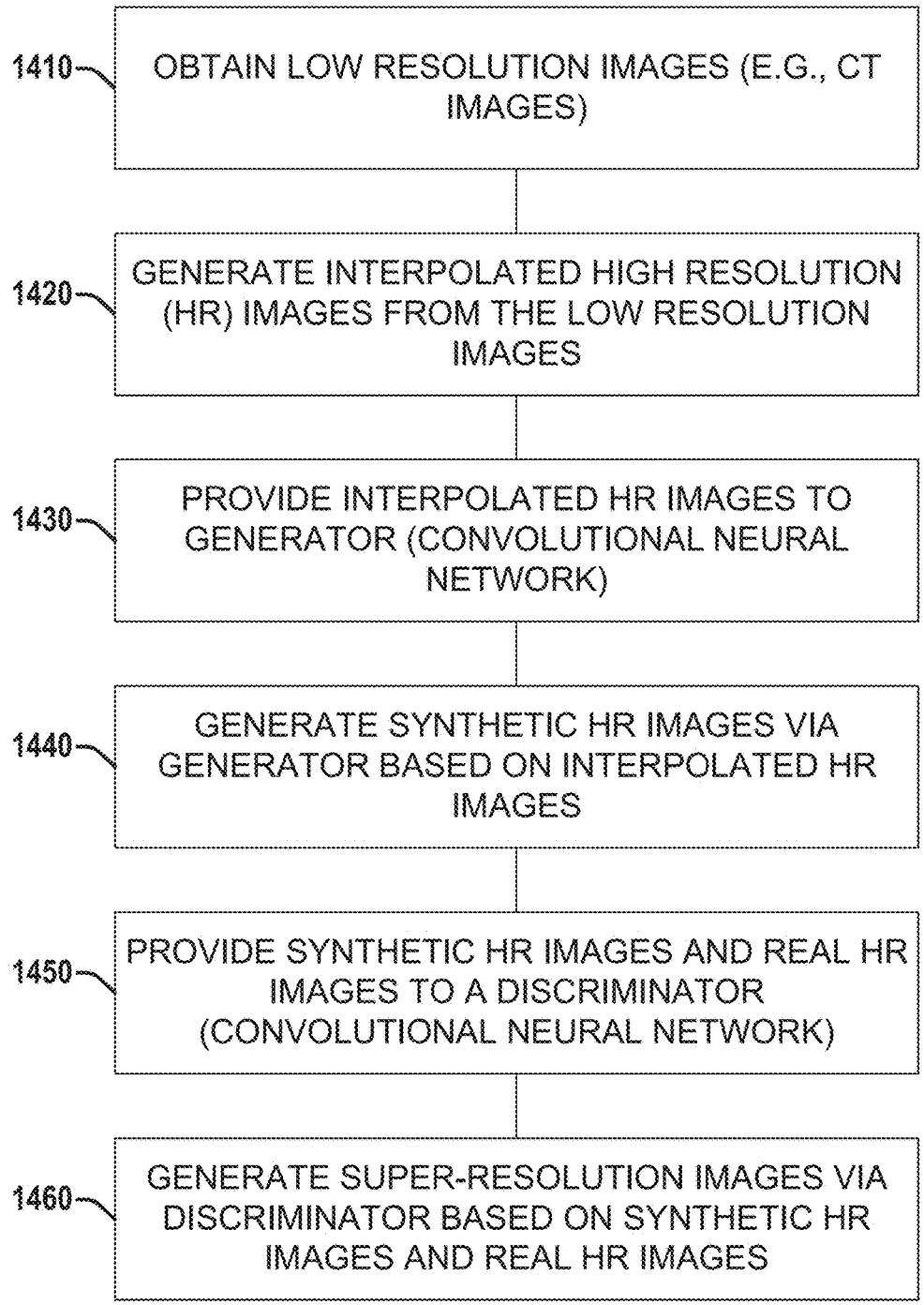
FIG. 14 illustrates a flow diagram showing an example method or set of operations that can be performed by one or more processors to improve calcification assessments via employing a generative adversarial network (GAN) to generate super-resolution CT images, according to various aspects discussed herein.

Referring to FIG. 14, illustrated is a flow diagram showing an example method or set of operations 1400 that can be performed by one or more processors to improve calcification assessments via employing a generative adversarial network (GAN) to generate super-resolution CT images, according to various aspects discussed herein.

The set of operations 1400 can comprise, at 1410, obtaining a set of low-resolution (LR) images (e.g., of a cardiac CT image volume). The set of LR images can be obtained via a system and/or apparatus implementing the set of operations 1400, or can be obtained from a separate medical imaging system. Additionally, the set of LR images can be accessed contemporaneously with or at any point prior to performing the set of operations 1400.

The set of operations 1400 can further comprise, at 1420, generating a set of interpolated high-resolution (HR) images from the set of LR images.

The set of operations 1400 can further comprise, at 1430, providing the interpolated HR images to a generator (e.g., a convolutional neural network (CNN), etc.).

The set of operations 1400 can further comprise, at 1440, generating a set of synthetic HR images via the generator based on the set of interpolated HR images.

The set of operations 1400 can further comprise, at 1450, providing the set of synthetic HR images and a set of real HR images to a discriminator (e.g., CNN, etc.).

The set of operations 1400 can further comprise, at 1460, generating a set of super-resolution images via the discriminator based on the set of synthetic HR images and the set of real HR images. The set of real HR images can be obtained via a system and/or apparatus implementing the set of operations 1400, or can be obtained from a separate medical imaging system. Additionally, the set of real HR images can be accessed contemporaneously with or at any point prior to performing the set of operations 1400.

Investigations using a phantom and cadaver heart show that corrections (deconvolution and partial volume correction) can improve accuracy and precision of mass scores from normal resolution scans (FIGS. 9-12). Blind deconvolution performed better than deconvolution with a measured point spread function (PSF) on phantom data, having large, highly calcified cylindrical objects, but more poorly on cadaver calcifications, with highly irregular shapes. Commercial software performed poorly as compared to our corrected results (not shown). FIG. 13 shows a flow diagram of deconvolution. FIG. 14 shows a diagram of the super-resolution GAN.

C. ICmore Single-Time-Point and Serial Assessments

Various embodiments can compute ICmore (Individual Calcification measures including morphological features and progression/regression/formation changes over time) features that include assessments of new, small calcifications that will likely negligibly contribute to whole heart Agatston, yet will likely be better indicators of disease progression and patient vulnerability than large, stable calcifications. Various embodiments can calculate traditional measures, including mass, Agatston, and volume, as well as density and mass moments on individual calcifications. In addition, embodiments can compute disease-sensitive, morphological features amenable for classification. Using registration methods, changes in ICmore measures between image volume time points can be computed. Since measurement repeatability is an issue with conventional slice thickness (e.g., as discussed in connection with FIGS. 9-12), various embodiments can employ corrections (e.g., super-resolution and partial volume, etc.), as described above. Using atlas labels, distances to the appropriate coronary ostium can be measured, which is a measure predictive of cardiac events.

For ICmore morphological features requiring a hard segmentation, a graphic object can be created in various embodiments using marching cubes or some variant, giving sub-voxel delineation of the surface. Various embodiments can use one or more of the following features: 3D extent; solidity; divergence; equivalent diameter; maximum intensity; form factor; convex hull; and bounding rectangle minimum, median, and max dimensions. To lessen effects of segmentation errors, grayscale-mass-moment measures can be computed by various embodiments. Using atlas labels, various embodiments can identify coronary ostia and weight calcifications by their distance to the corresponding ostium. For each linked calcification, various embodiments can collect ICmore measures at each time point, and can also determine change and/or percent change.

FIGS. 4, 5, and 7-12 relate to aspects discussed in this section. These figures demonstrate calcification detection and morphology (FIGS. 4 and 5), changes of registered calcifications over time (FIGS. 7 and 8), and repeatability following corrections (FIGS. 9-12).

Example features that can be used by various embodiments in single and/or serial time point assessment can comprise one or more of: (1) one or more intensity features such as (a) max/mean/min intensity in the calcified region, (b) weighted centroid, or (c) gradient of the calcified region; (2) one or more shape/size features such as (a) centroid, (b)

volume, (c) orientation, (d) surface area, (e) equivalent diameter of same size sphere, or (f) bounding box location and size; or (3) one or more location features such as (a) Vascular territory of the heart such as RCA, LAD, LM, or LCX or (b) distance between the centroid of calcification and aortic root.

For serial time point assessment of progression over time, various embodiments can track one or more of these features across different time points for the same patient. Based on single and/or serial assessment, various embodiments can generate a risk prediction model which predicts a patient's possibility of having adverse cardiovascular event (including heart attack, chest pain, stroke etc.) using the ICmore features given.

Additionally or alternatively, various embodiments can employ deep learning. For example, various embodiments can extract deep features from each time point by using a pretrained convolutional neural network (e.g., such as ResNet50, Vgg16, or DenseNet-169). For each individual calcification, a bounding box can be constructed which is centered at the calcification. ICmore deep features of each calcification can be extract from the corresponding bounding box.

D. Machine Learning to Improve Cardiovascular Risk Assessments and Effects of Drugs, Genes, Drugs, Genes, Environment, and Disease Confounds As compared to whole heart Agatston, ICmore features are anticipated to improve cardiovascular assessments. Using a dataset such as the 30-year Coronary Artery Risk Development in Young Adults (CARDIA) study, the ability of ICmore features to predict adverse cardiovascular events can be determined. Using a dataset such as the Stopping Atherosclerosis and Treating Unhealthy Bone with RosuvastatiN in HIV infection (SATURN-HIV) study, it can be determined if changes coincident with drug treatment (rosuvastatin) can be seen in ICmore features. These datasets can enable the creation of classifiers and regressions which can be employed in various embodiments to determine the effects of one or more of drugs, genes, environment, and disease prognosis on ICmore features.

Results in FIGS. 4-12 relate to aspects discussed in this section.

Details. For various embodiments, a classifier can be created for a dataset such as CARDIA, using standard approaches. In some embodiments, to determine the best ICmore features, their quality can be ranked based on change over repeat ratios (CRRs), as determined from the average signed or standard deviation of differences between time points to the standard deviation of differences at the same time point. In the same or other embodiments, standard approaches (e.g., mRMR and Wilcoxon) can also be employed. A classifier such as random forest or SVM can be employed. With 5-fold cross-validation on balanced data from cohorts, the ability of classifiers to predict an adverse event within a given time window can be determined. Performance metrics (e.g., ROC AUC, sensitivity/specificity, and F) can be reported across test folds to indicate the confidence in assessments. Confidence intervals from cross-validation results can be reported.

In various embodiments, regression can be employed as an alternative to a binary classifier. Statistics-based regression formulas can be used by some embodiments to predict risks of adverse events attributable to ICmore assessments. Regression can also be done in some embodiments using approaches such as SVM regression.

As an example, statistical evaluation application to SATURN study data is described. Various embodiments can use multifactor, univariate and multivariate (general/generalized) linear mixed-effects (LME) models with random intercepts and slopes. In various embodiments, univariate models can be built to examine the statin effect on each ICmore measure as well as whole heart Agatston for #2-#4. Multivariate LME models can then be employed with multifactors that can comprise one or more of treatment, age, sex, race, BMI, insulin resistance, baseline measure, or calcification grouping (small, medium, large). Various embodiments can determine interactions between treatment and sub-groups of interest. Random effects in the model can account for variations between individuals and correlations within individual serial measurements. Various embodiments can use both a structured and unstructured variance-covariance matrix, as recommended for growth curves. The structured variance-covariance can be examined based on the fit to data. The unadjusted and adjusted treatment effects can be estimated from the standard and multifactor models using restricted maximum likelihood and performing pre-transformation of data as appropriate. Using multifactor models helps with controlling subgroup differences and heterogeneities and provides inferences specific for each subgroup. To compare the quality of each ICmore measure and whole heart measure, their changes over time can be compared for different subgroups.

Another option employable by various embodiments is a neural network approach. With the ICmore features from individual calcification, a long-short term memory networks (LSTMs) can be trained as classifier for patient with different numbers of calcification. With LSTMs, each ICmore feature map of individual calcification can be fed into a repeating module of LSTM. The repeating module can then be trained for classification, and can be employed in various embodiments.

Additional Embodiments

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods 100, 200, 300, 1300, 1400, or any other methods or operations described herein. While executable instructions associated with the listed methods are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein relate to training and/or employing embodiments that facilitate determination of risk of an adverse event based on features of arterial calcification in a CT image volume that are not perceivable by the human eye, and involve computation that cannot be practically performed in the human mind. As one example, machine learning and/or deep learning classifiers as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then be used and applied to create desired results more accurately, more consistently, and with greater reliability than existing approaches, thereby producing the technical effect of improving the performance of the machine, computer, or system with which embodiments are implemented.

Figure 15:
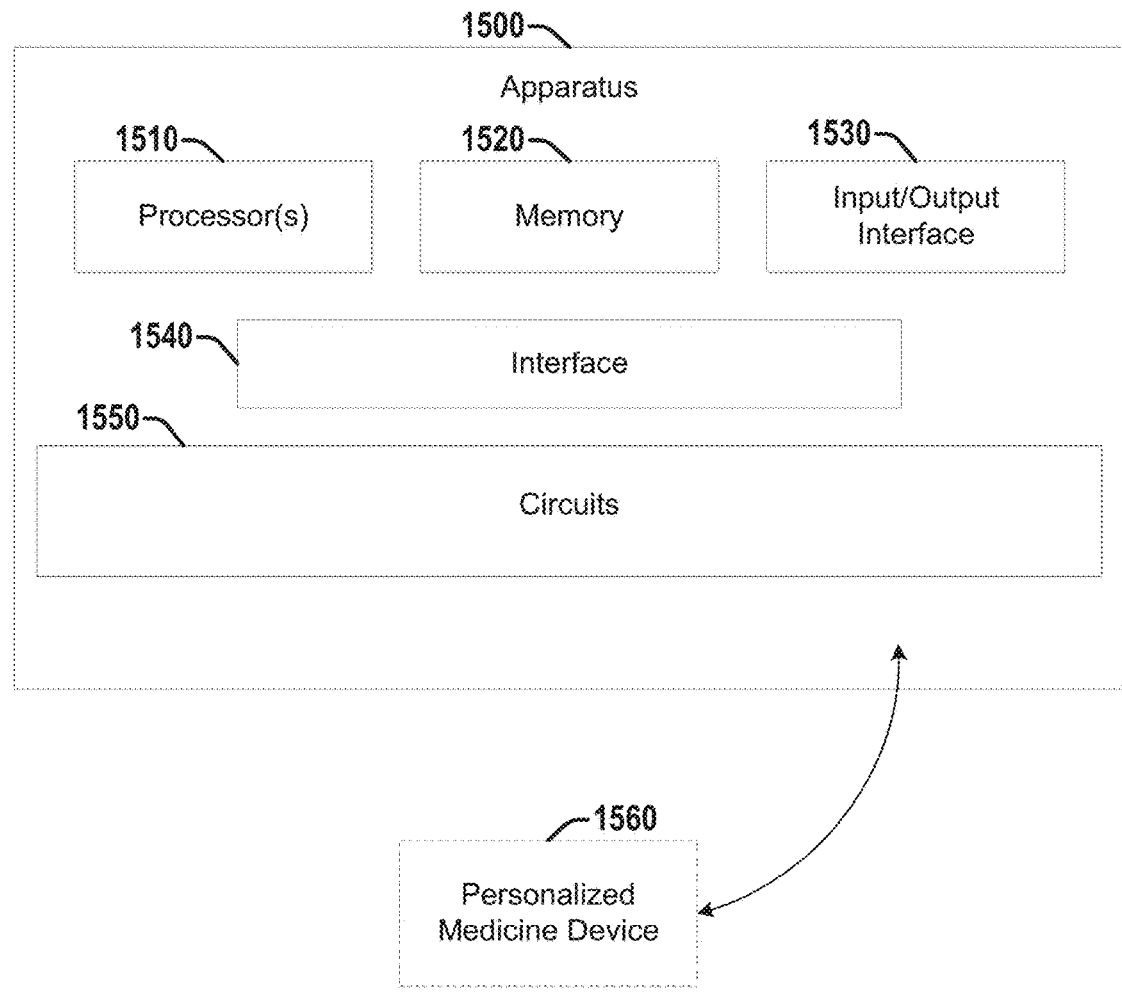
FIG. 15 illustrates a diagram of an example apparatus that can facilitate assessment (e.g., single or serial) of arterial calcification and/or training a machine learning (ML) or deep learning (DL) model to assess arterial calcification, according to various embodiments discussed herein.

Referring to FIG. 15, illustrated is a diagram of an example apparatus 1500 that can facilitate assessment (e.g., single or serial) of arterial calcification and/or training a machine learning (ML) or deep learning (DL) model to assess arterial calcification, according to various embodiments discussed herein. Apparatus 1500 can be configured to perform various techniques discussed herein, for example, various operations discussed in connection with sets of operations 100, 200, 300, 1300 and/or 1400. Apparatus 1500 comprises one or more processors 1510. Apparatus 1500 also comprises a memory 1520. Processor(s) 1510 can, in various embodiments, comprise circuitry such as, but not limited to, one or more single-core or multi-core processors. Processor(s) 1510 can include any combination of general-purpose processors and dedicated processors (e.g., graphics processors, application processors, etc.). The processor(s) can be coupled with and/or can comprise memory (e.g., of memory 1520) or storage and can be configured to execute instructions stored in the memory 1520 or storage to enable various apparatus, applications, or operating systems to perform operations and/or methods discussed herein. Memory 1520 can be configured to store a image volume (e.g., CT, MRI, etc.) of arterial calcification, for example, a CT image volume of coronary artery calcification. Each of the image(s) of the image volume can comprise a plurality of pixels or voxels, each pixel or voxel having an associated intensity. Memory 1520 can be further configured to store additional data involved in performing operations discussed herein, such as for assessment (e.g., single or serial) of arterial calcification and/or training a ML or DL model to assess arterial calcification, as discussed in greater detail herein.

Apparatus 1500 also comprises an input/output (I/O) interface 1530 (e.g., associated with one or more I/O devices), a set of circuits 1550, and an interface 1540 that connects the processor 1510, the memory 1520, the I/O interface 1530, and the set of circuits 1550. I/O interface 1530 can be configured to transfer data between memory 1520, processor 1510, circuits 1550, and external devices, for example, a medical imaging device (e.g., CT system or apparatus, etc.), and/or one or more remote devices for receiving inputs and/or providing outputs to a clinician, patient, etc., such as optional personalized medicine device 1560.

The processor(s) 1510 and/or one or more circuits of the set of circuits 1550 can be configured to receive a CT image volume (e.g., from memory 1520 or from an external device, etc.). The CT image volume can comprise an image volume of arterial calcification, such as a CT image volume of coronary artery calcification.

The processor(s) 1510 and/or one or more circuits of the set of circuits 1550 can perform one or more acts associated with a method or set of operations discussed herein, such as set of operations 100, 200, 300, 1300, or 1400. In various embodiments, different acts (e.g., different operations of a set of operations) can be performed by the same or different processor(s) 1510 and/or one or more circuits of the set of circuits 1550.

Apparatus 1500 can optionally further comprise personalized medicine device 1560. Apparatus 1500 can be configured to provide the predicted risk of adverse event(s) and/or risk stratification report, or other data to personalized medicine device 1560. Personalized medicine device 1560 may be, for example, a computer assisted diagnosis (CADx) system or other type of personalized medicine device that can be used to facilitate monitoring and/or treatment of an associated medical condition. In some embodiments, processor(s) 1510 and/or one or more circuits of the set of circuits 1550 can be further configured to control personalized medicine device 1560 to display the risk stratification report, predicted risk(s) of adverse event(s), or other data on a computer monitor, a smartphone display, a tablet display, or other displays.

Examples herein can include subject matter such as an apparatus, a quantitative perfusion measurement system, a CT system, an MRI system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for generating system-independent quantitative perfusion measurements, according to embodiments and examples described.

Example 1 is a non-transitory computer-readable medium storing computer-executable instructions that, when executed, cause a processor to perform operations, comprising: accessing a Computed Tomography (CT) image volume of at least one artery of a patient; identifying one or calcification candidates based on the CT image volume; identifying one or more territories of the at least one artery based on a registration of an atlas to the CT image volume; calculating, for each territory of the one or more territories, an associated calcium score for that territory, based on the registration of the atlas to the CT image volume; extracting, for each calcification candidate of the one or more calcification candidates, one or more associated features for that calcification candidate; providing the one or more associated features for each calcification candidate to a pretrained model, wherein the pretrained model is one of a pretrained Machine Learning model or a pretrained Deep Learning model; and generating a risk stratification report for the patient via the pretrained model, wherein the risk stratification report indicates a probability associated with each of one or more adverse events.

Example 2 comprises the subject matter of any variation of any of example(s) 1, wherein the operations further comprise performing pre-processing on the CT image volume to generate a pre-processed CT image volume, wherein identifying the one or more calcification candidates based on the CT image volume comprises identifying the one or more calcification candidates based on the pre-processed CT image volume.

Example 3 comprises the subject matter of any variation of any of example(s) 2, wherein performing pre-processing on the CT image volume comprises performing a partial volume correction on the CT image volume.

Example 4 comprises the subject matter of any variation of any of example(s) 2-3, wherein performing pre-processing on the CT image volume comprises performing a deconvolution on the CT image volume.

Example 5 comprises the subject matter of any variation of any of example(s) 2-4, wherein performing pre-processing on the CT image volume comprises generating a super-resolution CT image volume based on the CT image volume.

Example 6 comprises the subject matter of any variation of any of example(s) 1-5, wherein identifying the one or more territories of the at least one artery based on the registration of the atlas to the CT image volume: registering a plurality of potential atlases to a down-sampled version of the CT image volume; computing, for each potential atlas of the plurality of potential atlases, an associated normalized cross-correlation for that potential atlas; selecting, as the atlas, the potential atlas with a best associated normalized cross-correlation of the plurality of potential atlases; and registering the atlas to the CT image volume at full resolution.

Example 7 comprises the subject matter of any variation of any of example(s) 1-6, wherein for each calcification candidate of the one or more calcification candidates, the one or more associated features for that calcification candidate comprise one or more intensity features for that calcification candidate, wherein the one or more intensity features for that calcification candidate comprise one or more of: a maximum intensity in that calcification candidate, a mean intensity in that calcification candidate, a minimum intensity in that calcification candidate, a weighted centroid of that calcification candidate, or a gradient of that calcification candidate.

Example 8 comprises the subject matter of any variation of any of example(s) 1-7, wherein for each calcification candidate of the one or more calcification candidates, the one or more associated features for that calcification candidate comprise one or more shape or size features for that calcification candidate, wherein the one or more shape or size features for that calcification candidate comprise one or more of: a centroid of that calcification candidate, a volume of that calcification candidate, an orientation of that calcification candidate, a surface area of that calcification candidate, an equivalent diameter of a sphere with a volume equal to that calcification candidate, a bounding box location of that calcification candidate, or a bounding box size of that calcification candidate.

Example 9 comprises the subject matter of any variation of any of example(s) 1-8, wherein for each calcification candidate of the one or more calcification candidates, the one or more associated features for that calcification candidate comprise one or more location features for that calcification candidate, wherein the one or more location features for that calcification candidate comprise one or more of: a vascular territory of that calcification candidate or a distance between an aortic root and a centroid of calcification of that calcification candidate.

Example 10 comprises the subject matter of any variation of any of example(s) 1-9, wherein for each calcification candidate of the one or more calcification candidates, the one or more associated features for that calcification candidate comprise one or more deep learned features associated with that calcification candidate.

Example 11 comprises the subject matter of any variation of any of example(s) 1-10, wherein the pretrained model comprises one or more of a classifier, a regression model, or a neural network.

Example 12 comprises the subject matter of any variation of any of example(s) 1-11, wherein the at least one artery comprises at least one coronary artery.

Example 13 is a non-transitory computer-readable medium storing computer-executable instructions that, when executed, cause a processor to perform operations, comprising: accessing, for each of a plurality of time points, an associated Computed Tomography (CT) image volume for that time point, wherein the associated CT image volume for each time point of the plurality of time points is an associated CT image volume of at least one artery of a patient; calculating, for each territory of one or more territories of the at least one artery, an associated calcium score for that territory for each time point, based on the associated CT image volume for that time point; extracting, from each calcified region of one or more calcified regions of the at least one artery, one or more associated features for that calcified region for each time point, from the associated CT image volume for that time point; co-registering the associated CT image volume for each time point of the plurality of time points; analyzing, for each calcified region of the one or more calcified regions, changes in the associated features for that calcified region over the plurality of time points; and predicting, via a pretrained model, an associated risk for each adverse event of one or more adverse events, based on one or more of the associated calcium score for each territory of the one or more territories and for each time point of the plurality of time points, or the changes in the associated features for each calcified region of the one or more calcified regions over the plurality of time points, wherein the pretrained model is one of a pretrained Machine Learning model or a pretrained Deep Learning model.

Example 14 comprises the subject matter of any variation of any of example(s) 13, wherein co-registering the associated CT image volume for each time point of the plurality of time points comprises registering the associated CT image volume for each time point of the plurality of time points other than a last time point of the plurality of time points to the associated CT image volume for the last time point.

Example 15 comprises the subject matter of any variation of any of example(s) 14, wherein, for each time point of the plurality of time points other than the last time point, registering the associated CT image volume for that time point to the associated CT image volume for the last time point comprises: performing an initial normalized-cross-correlation rigid body registration of the associated CT image volume for that time point to the associated CT image volume for the last time point; and based on the initial normalized-cross-correlation rigid body registration, aligning the one or more calcification regions in the associated CT image volume for that time point with the one or more calcification regions in the associated CT image volume for the last time point via an iterative closest point (ICP) algorithm, wherein the ICP algorithm is performed in a higher-dimensional space involving one or more morphological features assigned to each of the one or more calcification regions.

Example 16 comprises the subject matter of any variation of any of example(s) 13-15, wherein the operations further comprise, for each time point of the plurality of time points, performing pre-processing on the associated CT image volume for that time point to generate an associated pre-processed CT image volume for that time point, wherein performing pre-processing on the associated CT image volume for that time point comprises one or more of: performing a partial volume correction on the associated CT image volume for that time point, performing a deconvolution on the associated CT image volume for that time point, or generating an associated super-resolution CT image volume for that time point based on the associated CT image volume for that time point.

Example 17 comprises the subject matter of any variation of any of example(s) 13-16, wherein for each calcified region of the one or more calcified regions, the one or more associated features for that calcified region for each time point comprise one or more intensity features for that calcified region for that time point, wherein the one or more intensity features for that calcified region for that time point comprise one or more of: a maximum intensity in that calcified region for that time point, a mean intensity in that calcified region for that time point, a minimum intensity in that calcified region for that time point, a weighted centroid of that calcified region for that time point, or a gradient of that calcified region for that time point.

Example 18 comprises the subject matter of any variation of any of example(s) 13-17, wherein for each calcified region of the one or more calcified regions, the one or more associated features for that calcified region for each time point comprise one or more shape or size features for that calcified region for that time point, wherein the one or more shape or size features for that calcified region for that time point comprise one or more of: a centroid of that that calcified region for that time point, a volume of that that calcified region for that time point, an orientation of that that calcified region for that time point, a surface area of that that calcified region for that time point, an equivalent diameter of a sphere with a volume equal to that that calcified region for that time point, a bounding box location of that that calcified region for that time point, or a bounding box size of that that calcified region for that time point.

Example 19 comprises the subject matter of any variation of any of example(s) 13-18, wherein for each calcified region of the one or more calcified regions, the one or more associated features for that calcified region for each time point comprise one or more location features for that calcified region for that time point, wherein the one or more location features for that calcified region for that time point comprise one or more of: a vascular territory of that that calcified region for that time point or a distance between an aortic root and a centroid of calcification of that that calcified region for that time point.

Example 20 comprises the subject matter of any variation of any of example(s) 13-19, wherein for each calcified region of the one or more calcified regions, the one or more associated features for that calcified region for each time point comprise one or more deep learned features associated with that calcified region for that time point.

Example 21 is a non-transitory computer-readable medium storing computer-executable instructions that, when executed, cause a processor to perform operations, comprising: accessing a plurality of Computed Tomography (CT) image volumes associated with at least one artery; obtaining, for each CT image volume of the plurality of CT image volumes, a clinical outcome of an associated patient for that CT image volume; identifying, based on each CT image volume of the plurality of CT image volumes, one or more associated calcification candidate regions in that CT image volume; extracting, from each associated calcification candidate region of the one or more associated calcification candidate regions of each CT image volume of the plurality of CT image volumes, one or more associated features for that associated calcification candidate region of that CT image volume; and for each CT image volume of the plurality of CT image volumes, training a model based on the clinical outcome of the associated patient for that CT image volume and the one or more associated features for each associated calcification candidate region of the one or more associated calcification candidate regions of that CT image volume, wherein the model is one of a Machine Learning model or a Deep Learning model.

Example 22 comprises the subject matter of any variation of any of example(s) 21, wherein the model comprises one or more of a classifier, a regression model, or a neural network.

Example 23 comprises the subject matter of any variation of any of example(s) 21-22, wherein the associated features are selected from a larger set of potential features based on ranking the larger set of potential features based on one of: a quality based on a change over repeat ratios (CRRs), a minimum redundancy maximum relevance (mRMR) approach, or a Wilcoxon approach.

Example 24 comprises an apparatus comprising means for executing any of the described operations of examples 1-23.

Example 25 comprises a machine readable medium that stores instructions for execution by a processor to perform any of the described operations of examples 1-23.

Example 26 comprises an apparatus comprising: a memory; and one or more processors configured to: perform any of the described operations of examples 1-23.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action(s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable medium storing computer-executable instructions that, when executed, cause a processor to perform operations, comprising:
   accessing a Computed Tomography (CT) image volume of at least one artery of a patient;
   identifying one or more calcification candidates based on the CT image volume;
   identifying one or more territories of the at least one artery based on a registration of an atlas to the CT image volume;
   calculating, for each territory of the one or more territories, an associated calcium score for that territory, based on the registration of the atlas to the CT image volume;
   extracting, for each calcification candidate of the one or more calcification candidates, one or more associated features for that calcification candidate;
   providing the one or more associated features for each calcification candidate to a pretrained model, wherein the pretrained model is one of a pretrained Machine Learning model or a pretrained Deep Learning model; and
   making a risk assessment based upon the calcium score associated with a territory of the one or more territories, and not upon a whole heart calcium score, and also based upon the one or more associated features.

2. The non-transitory computer-readable medium of claim 1, wherein the operations further comprise performing pre-processing on the CT image volume to generate a pre-processed CT image volume, wherein identifying the one or more calcification candidates based on the CT image volume comprises identifying the one or more calcification candidates based on the pre-processed CT image volume.

3. The non-transitory computer-readable medium of claim 2, wherein performing pre-processing on the CT image volume comprises performing a partial volume correction on the CT image volume, performing a deconvolution on the CT image volume, or generating a super-resolution CT image volume based on the CT image volume.

4. The non-transitory computer-readable medium of claim 2,
   wherein the CT image volume comprises images of an artery taken at different times; and
   wherein the CT image volumes acquired at the different times are co-registered to the atlas.

5. The non-transitory computer-readable medium of claim 2, further comprising:
   performing a partial volume correction on the one or more calcification candidates after identifying one or more territories.

6. The non-transitory computer-readable medium of claim 1, wherein identifying the one or more territories of the at least one artery based on the registration of the atlas to the CT image volume:
   registering a plurality of potential atlases to a down-sampled version of the CT image volume;
   computing, for each potential atlas of the plurality of potential atlases, an associated normalized cross-correlation for that potential atlas;
   selecting, as the atlas, the potential atlas with a best associated normalized cross-correlation of the plurality of potential atlases; and
   registering the atlas to the CT image volume at full resolution.

7. The non-transitory computer-readable medium of claim 1, wherein for each calcification candidate of the one or more calcification candidates, the one or more associated features for that calcification candidate comprise one or more intensity features for that calcification candidate, wherein the one or more intensity features for that calcification candidate comprise one or more of: a maximum intensity in that calcification candidate, a mean intensity in that calcification candidate, a minimum intensity in that calcification candidate, a weighted centroid of that calcification candidate, or a gradient of that calcification candidate.

8. The non-transitory computer-readable medium of claim 1, wherein for each calcification candidate of the one or more calcification candidates, the one or more associated features for that calcification candidate comprise one or more shape or size features for that calcification candidate, wherein the one or more shape or size features for that calcification candidate comprise one or more of: a centroid of that calcification candidate, a volume of that calcification candidate, an orientation of that calcification candidate, a surface area of that calcification candidate, an equivalent diameter of a sphere with a volume equal to that calcification candidate, a bounding box location of that calcification candidate, or a bounding box size of that calcification candidate.

9. The non-transitory computer-readable medium of claim 1, wherein for each calcification candidate of the one or more calcification candidates, the one or more associated features for that calcification candidate comprise one or more location features for that calcification candidate, wherein the one or more location features for that calcification candidate comprise one or more of: a vascular territory of that calcification candidate or a distance between an aortic root and a centroid of calcification of that calcification candidate.

10. The non-transitory computer-readable medium of claim 1, wherein for each calcification candidate of the one or more calcification candidates, the one or more associated features for that calcification candidate comprise one or more deep learned features associated with that calcification candidate.

11. The non-transitory computer-readable medium of claim 1, wherein the CT image volume comprises images of an artery taken at two or more different time points.

12. The non-transitory computer-readable medium of claim 11, further comprising:
analyzing changes in the one or more associated features between the two or more different time points; and
making the risk assessment based on the analyzed changes in the one or more associated features.

13. A non-transitory computer-readable medium storing computer-executable instructions that, when executed, cause a processor to perform operations, comprising:
accessing, for each of a plurality of time points respectively occurring at different times, an associated Computed Tomography (CT) image volume for that time point, wherein the associated CT image volume for each time point of the plurality of time points is an associated CT image volume of at least one artery of a patient;
calculating, for each territory of one or more territories of the at least one artery, an associated calcium score for that territory for each time point, based on the associated CT image volume for that time point;
extracting, from each calcified region of one or more calcified regions of the at least one artery, one or more associated features for that calcified region for each time point, from the associated CT image volume for that time point;
co-registering the associated CT image volume for each time point of the plurality of time points;
analyzing, for each calcified region of the one or more calcified regions, changes in the associated features for that calcified region over the plurality of time points; and
predicting, via a pretrained model, an associated risk for each adverse event of one or more adverse events, based on one or more of the associated calcium score for each territory of the one or more territories and for each time point of the plurality of time points, or the changes in the associated features for each calcified region of the one or more calcified regions over the plurality of time points, wherein the pretrained model is one of a pretrained Machine Learning model or a pretrained Deep Learning model.

14. The non-transitory computer-readable medium of claim 13, wherein co-registering the associated CT image volume for each time point of the plurality of time points comprises registering the associated CT image volume for each time point of the plurality of time points other than a last time point of the plurality of time points to the associated CT image volume for the last time point.

15. The non-transitory computer-readable medium of claim 14, wherein, for each time point of the plurality of time points other than the last time point, registering the associated CT image volume for that time point to the associated CT image volume for the last time point comprises:

performing an initial normalized-cross-correlation rigid body registration of the associated CT image volume for that time point to the associated CT image volume for the last time point; and
based on the initial normalized-cross-correlation rigid body registration, aligning the one or more calcified regions in the associated CT image volume for that time point with the one or more calcified regions in the associated CT image volume for the last time point via an iterative closest point (ICP) algorithm, wherein the ICP algorithm is performed in a higher-dimensional space involving one or more morphological features assigned to each of the one or more calcified regions.

16. The non-transitory computer-readable medium of claim 13, wherein the operations further comprise, for each time point of the plurality of time points, performing pre-processing on the associated CT image volume for that time point to generate an associated pre-processed CT image volume for that time point, wherein performing pre-processing on the associated CT image volume for that time point comprises one or more of: performing a partial volume correction on the associated CT image volume for that time point, performing a deconvolution on the associated CT image volume for that time point, or generating an associated super-resolution CT image volume for that time point based on the associated CT image volume for that time point.

17. The non-transitory computer-readable medium of claim 13, wherein for each calcified region of the one or more calcified regions, the one or more associated features for that calcified region for each time point comprise one or more intensity features for that calcified region for that time point, wherein the one or more intensity features for that calcified region for that time point comprise one or more of: a maximum intensity in that calcified region for that time point, a mean intensity in that calcified region for that time point, a minimum intensity in that calcified region for that time point, a weighted centroid of that calcified region for that time point, or a gradient of that calcified region for that time point.

18. The non-transitory computer-readable medium of claim 13, wherein for each calcified region of the one or more calcified regions, the one or more associated features for that calcified region for each time point comprise one or more shape or size features for that calcified region for that time point, wherein the one or more shape or size features for that calcified region for that time point comprise one or more of: a centroid of that that calcified region for that time point, a volume of that that calcified region for that time point, an orientation of that that calcified region for that time point, a surface area of that that calcified region for that time point, an equivalent diameter of a sphere with a volume equal to that that calcified region for that time point, a bounding box location of that that calcified region for that time point, or a bounding box size of that that calcified region for that time point.

19. The non-transitory computer-readable medium of claim 13, wherein for each calcified region of the one or more calcified regions, the one or more associated features for that calcified region for each time point comprise one or more location features for that calcified region for that time point, wherein the one or more location features for that calcified region for that time point comprise one or more of: a vascular territory of that that calcified region for that time point or a distance between an aortic root and a centroid of calcification of that that calcified region for that time point.

20. A non-transitory computer-readable medium storing computer-executable instructions that, when executed, cause a processor to perform operations, comprising:
- accessing a plurality of Computed Tomography (CT) image volumes associated with at least one artery;
- obtaining, for each CT image volume of the plurality of CT image volumes, a clinical outcome of an associated patient for that CT image volume;
- identifying, based on each CT image volume of the plurality of CT image volumes, one or more associated calcification candidate regions in that CT image volume;
- extracting, from each associated calcification candidate region of the one or more associated calcification candidate regions of each CT image volume of the plurality of CT image volumes, one or more associated features for that associated calcification candidate region of that CT image volume; and
- for each CT image volume of the plurality of CT image volumes, training a model based on the clinical outcome of the associated patient for that CT image volume and the one or more associated features for each associated calcification candidate region of the one or more associated calcification candidate regions of that CT image volume, wherein the model is one of a Machine Learning model or a Deep Learning model.

21. The non-transitory computer-readable medium of claim 20, further comprising:
- identifying the one or more associated calcification candidate regions based on a registration of an atlas to the CT image volume;
- performing pre-processing on the CT image volume prior to registration of the atlas to the CT image volume; and
- performing a partial volume correction on the one or more associated calcification candidate regions after identifying the one or more associated calcification candidate regions.

22. The non-transitory computer-readable medium of claim 20, wherein the one or more associated features of the associated calcification candidate region comprise a maximum, mean, or minimum intensity in the associated calcification candidate region, a weighted centroid of the associated calcification candidate region, a gradient of the associated calcification candidate region, a centroid of the associated calcification candidate region, a volume of the associated calcification candidate region, an orientation of the associated calcification candidate region, a surface area of the associated calcification candidate region, an equivalent diameter of same size sphere of the associated calcification candidate region, a bounding box location and size of the associated calcification candidate region, a Vascular territory of a heart of the associated calcification candidate region, or a distance between a centroid of the associated calcification candidate region and an aortic root.

23. The non-transitory computer-readable medium of claim 20, wherein for each associated calcification candidate region of the one or more associated calcification candidate regions, the one or more associated features comprise one or more shape or size features for that associated calcification candidate region, wherein the one or more shape or size features for that associated calcification candidate region comprise one or more of: a centroid of that associated calcification candidate region, a volume of that associated calcification candidate region, an orientation of that associated calcification candidate region, a surface area of that associated calcification candidate region, an equivalent diameter of a sphere with a volume equal to that associated calcification candidate region, a bounding box location of that associated calcification candidate region, or a bounding box size of that associated calcification candidate region.

* * * * *